United States Patent
Gravel et al.

(10) Patent No.: US 6,458,764 B1
(45) Date of Patent: *Oct. 1, 2002

(54) GRF ANALOGS WITH INCREASED BIOLOGICAL POTENCY

(75) Inventors: Denis Gravel, St-Lambert; Abdelkrim Habi, Anjou; Paul Brazeau, Montréal, all of (CA)

(73) Assignee: Theratechnologies Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/389,486

(22) Filed: Sep. 3, 1999

Related U.S. Application Data

(63) Continuation-in-part of application No. 09/148,982, filed on Sep. 8, 1998, now Pat. No. 6,020,311, which is a continuation-in-part of application No. 08/702,113, filed on Aug. 23, 1996, now Pat. No. 5,939,386, and a continuation-in-part of application No. 08/702,114, filed on Aug. 23, 1996, now Pat. No. 5,861,379, which is a continuation-in-part of application No. 08/651,645, filed on May 22, 1996, now abandoned, which is a continuation-in-part of application No. 08/453,067, filed on May 26, 1995, now abandoned.

(51) Int. Cl.$^7$ .................. A61K 38/25; C07K 14/60

(52) U.S. Cl. .................. 514/12; 530/324; 530/399; 930/120

(58) Field of Search .................. 514/12; 530/324, 530/399; 930/120

(56) References Cited

U.S. PATENT DOCUMENTS 5,861,379 A * 1/1999 Ibea et al. .................. 514/12
5,939,386 A * 8/1999 Ibea et al. .................. 514/12
6,020,311 A * 2/2000 Brazeau et al. .................. 514/12

\* cited by examiner

*Primary Examiner*—Christopher S. F. Low
*Assistant Examiner*—Abdel A. Mohamed
(74) *Attorney, Agent, or Firm*—Crowell & Moring LLP

(57) ABSTRACT

The present invention relates to chimeric fatty body-GRF analogs with increased biological potency, their application as anabolic agents and in the diagnosis and treatment of growth hormone deficiencies. The chimeric fatty body-GRF analogs include an hydrophobic moiety (tail), and can be prepared, either by anchoring at least one hydrophobic tail to the GRF, in the chemical synthesis of GRF. The GRF analogs of the present invention are biodegradable, non-immunogenic and exhibit an improved anabolic potency with a reduced dosage and prolonged activity.

10 Claims, 10 Drawing Sheets

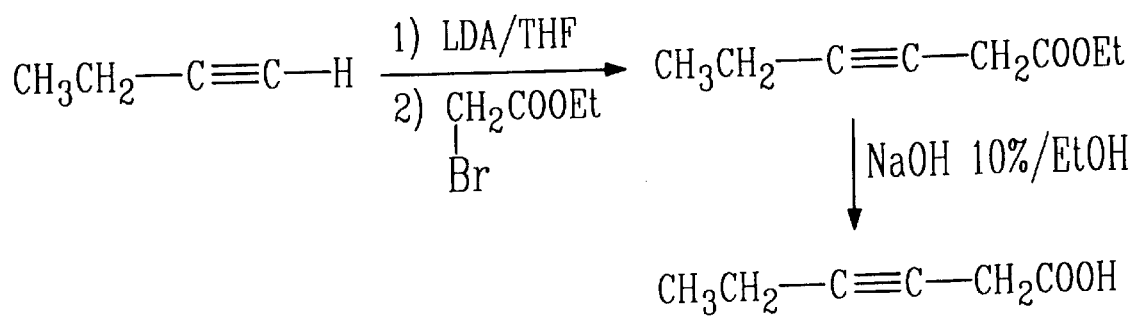
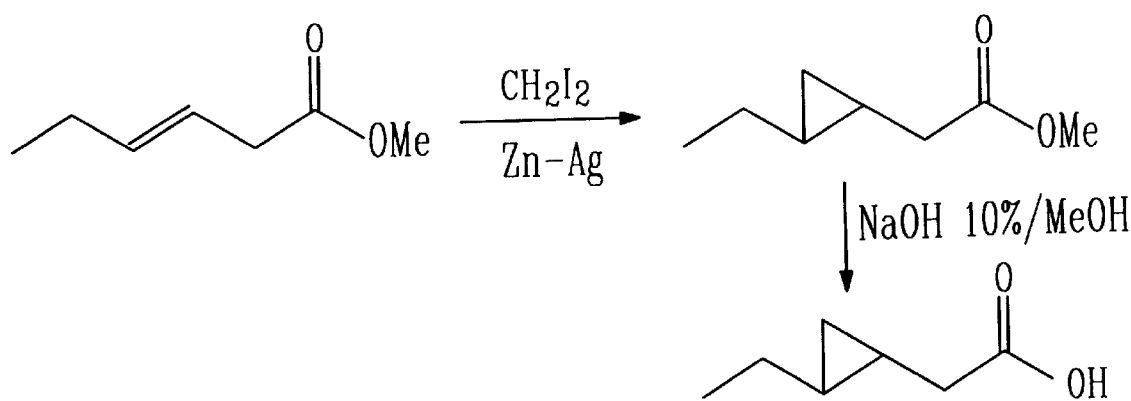
FIG. 6A

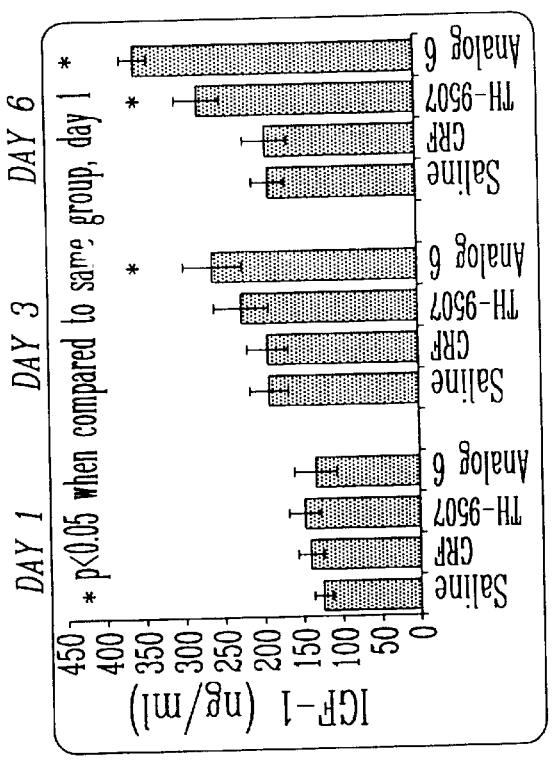
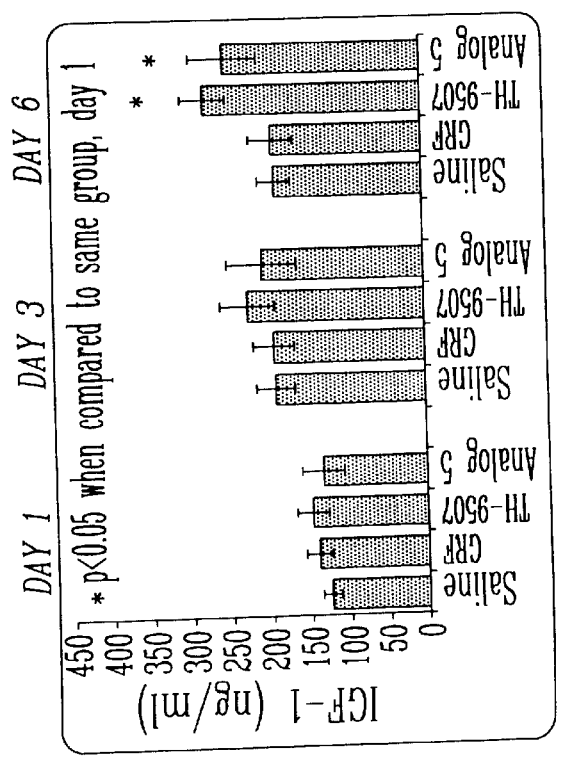
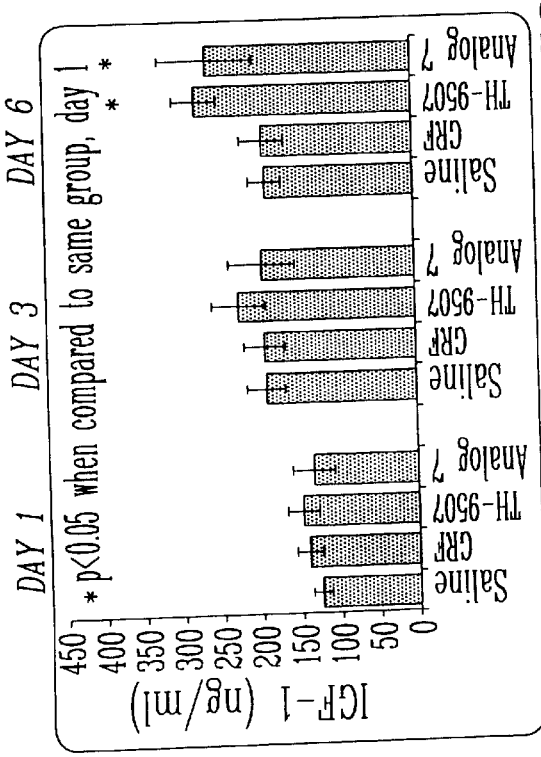
FIG. 7B

SEQUENCE LISTING

<160> NUMBER OF SEQ ID NOS: 2

<210> SEQ ID NO 1
<211> LENGTH: 44
<212> TYPE: PRT
<213> ORGANISM: Human GRF

<400> SEQUENCE: 1

Tyr Ala Asp Ala Ile Phe Thr Asn Ser Tyr Arg Lys Val Leu Gly Gln

```
                1               5                   10                  15
            Leu Ser Ala Arg Lys Leu Leu Gln Asp Ile Met Ser Arg Gln Gln Gly
                            20                  25                  30

Glu Ser Asn Gln Glu Arg Gly Ala Arg Ala Arg Leu
                            35                  40

<210> SEQ ID NO 2
            <211> LENGTH: 29
            <212> TYPE: PRT
            <213> ORGANISM: Active core of human GRF

<400> SEQUENCE: 2

Tyr Ala Asp Ala Ile Phe Thr Asn Ser Tyr Arg Lys Val Leu Gly Gln
              1             5                   10                  15

Leu Ser Ala Arg Lys Leu Leu Gln Asp Ile Met Ser Arg
                            20                  25
```

GRF ANALOGS WITH INCREASED BIOLOGICAL POTENCY

RELATED APPLICATIONS

This application is a continuation-in-part of application Ser. No. 09/148,982 filed on Sep. 8, 1998 which is now U.S. Pat. No. 6,020,311, which is a continuation-in-part application of application Ser. No. 08/702,113 filed on Aug. 23, 1996 and and which issued on Aug. 17, 1999 as U.S. Pat. No. 5,939,386 and Ser. No. 08/702,114 filed on Aug. 23, 1996 and which issued on Jan. 19, 1999 as U.S. Pat. No. 5,861,379; and which are continuations in part of application Ser. No. 08/651,645 filed on May 22, 1996, which is abandoned; and is a continuation-in-part of application Ser. No. 08/453,067 filed on May 26, 1995 and which is abandoned and all above applications are all incorporated herein by reference.

BACKGROUND OF THE INVENTION (a) Field of the Invention

The invention relates to hydrophobic GRF analogs with increased biological potency and prolonged activity, their application as anabolic agents and treatment of growth hormone deficiencies.

(b) Description of Prior Art

Growth hormone (GH) or somatotropin, secreted by the pituitary gland constitutes a family of hormones which biological activity is fundamental for the linear growth of a young organism but also for the maintenance of the integrity at its adult state. GH acts directly or indirectly on the peripheral organs by stimulating the synthesis of growth factors (insulin-like growth factor-I or IGF-I) or of their receptors (epidermal growth factor or EGF). The direct action of GH is of the type referred to as anti-insulinic, which favors the lipolysis at the level of adipose tissues. Through its action on IGF-I (somatomedin C) synthesis and secretion, GH stimulate the growth of the cartilage and the bones (structural growth), the protein synthesis and the cellular proliferation in multiple peripheral organs, including muscles and the skin. Through its biological activity, GH participates within adults in the maintenance of a protein anabolism state, and plays a primary role in the tissue regeneration phenomenon after a trauma.

The decrease of GH secretion with age, demonstrated in humans and animals, favors a metabolic shift towards catabolism which initiates or participates in the aging of an organism. The loss in muscle mass, the accumulation of adipose tissue, the bone demineralization, the loss of tissue regeneration capacity after an injury, which are observed in elderly, correlate with the decrease in the secretion of GH.

GH is thus a physiological anabolic agent absolutely necessary for the linear growth of children and which controls the protein metabolism in adults.

The secretion of GH by the pituitary gland is principally controlled by two hypothalamic peptides, somatostatin and growth hormone releasing factor (GRF). Somatostatin inhibits its secretion, whereas GRF stimulates it.

The human GH has been produced by genetic engineering for about ten years. Until recently most of the uses of GH were concerned with growth delay in children and now the uses of GH in adults are being studied. The pharmacological uses of GH and GRF may be classified in the following three major categories.

Children Growth

Treatments with recombinant human growth hormone have been shown to stimulate growth in children with pituitary dwarfism, renal insufficiencies, Turner's syndrome and short stature. Recombinant human GH is presently commercialized as an "orphan drug" in Europe and in the United States for children's growth retardation caused by a GH deficiency and for children's renal insufficiencies. The other uses are under clinical trial investigation.

Long Term Treatment for Adults and Elderly Patients

A decrease in GH secretion causes changes in body composition during aging. Preliminary studies of one-year treatment with recombinant human GH reported an increase in the muscle mass and in the thickness of skin, a decrease in fat mass with a slight increase in bone density in a population of aged patients. With respect to osteoporosis, recent studies suggest that recombinant human GH does not increase bone mineralization but it is suggested that it may prevent bone demineralization in post-menopausal women. Further studies are currently underway to demonstrate this theory.

Short Term Treatment in Adults and Elderly Patients

In preclinical and clinical studies, growth hormone has been shown to stimulate protein anabolism in wound and bone healing in cases of bum, AIDS and cancer.

GH and GRF are also intended for veterinary pharmacological uses. Both GH and GRF stimulate growth in pigs during its fattening period by favoring the deposition of muscle tissue instead of adipose tissue and increase milk production in cows, and this without any undesired side effects which would endanger the health of the animals, and without any residue in the meat or milk being produced. The bovine somatotropin (BST) is presently commercialized in the United States.

Most of the clinical studies undertaken were conducted with recombinant GH. GRF is considered as a second generation product destined to replace, in the near future, the use of GH in most instances. Accordingly, the use of GRF presents a number of advantages over the use of GH per se.

cl Physiological Advantages

Growth hormone (GH) is secreted by the pituitary gland in a pulse fashion. Since this rhythm of secretion is crucial for an optimal biological activity, the administration of GH to correspond to its natural mode of secretion is difficult to achieve. When GRF is administered in a continuous fashion as a slow releasing preparation or as an infusion, it increases GH secretion while respecting its pulsatility.

The recombinant GH which is presently commercialized is the 22 kDa form whereas GRF induces the synthesis and secretion from the pituitary gland of all the chemical isomers of GH which participate in a wider range of biological activities.

A treatment with GH results in a decreased capacity of the pituitary gland to secrete endogenous growth hormone, and the GH response to GRF is diminished after such a treatment. On the contrary, a treatment with GRF does not present this disadvantage, its trophic action on the pituitary gland increases this gland's secreting capacity in normal animals and in patients with somatotroph insufficiency.

Economical Advantages

The production of GH by genetic engineering is very expensive for clinical use. In particular, there are risks of contamination of these commercial preparations with material from the bacterial strain used. These bacterial contaminants may be pyrogens or may result in immunogenic reactions in patients. The purification of the recombinant product is carried out by following a plurality of successive chromatography steps. The drastic purity criteria imposed by regulatory agencies necessitate multiple quality control steps.

On the other hand, the synthesis of GRF is of chemical nature. The synthesis is carried out in a solid phase and its purification is done in a single step using high performance liquid chromatography (HPLC). Also the quantity of GRF to be administered is much less than the quantity of GH for the same biological result.

Even with all these advantages, GRF is still not commercialized as a therapeutic agent to date, mainly because of its instability. The human GRF is a peptide of 44 amino acids of the following sequence:

```
                                           (SEQ ID NO:1)
Tyr Ala Asp Ala Ile Phe Thr Asn Ser Tyr Arg Lys
1               5                   10

Val Leu Gly Gln Leu Ser Ala Arg Lys Leu Leu Gln
            15                  20

Asp Ile Met Ser Arg Gln Gln Gly Glu Ser Asn Gln
25                  30                      35

Glu Arg Gly Ala Arg Ala Arg Leu-NH₂.
            40
```

The minimum active core is hGRF (1-29)NH$_2$

```
                                           (SEQ ID NO:2)
Tyr Ala Asp Ala Ile Phe Thr Asn Ser Tyr Arg Lys
1               5                   10

Val Leu Gly Gln Leu Ser Ala Arg Lys Leu Leu Gln
            15                  20

Asp Ile Met Ser Arg.
25
```

As for many peptides, hGRF (1-29)NH$_2$ is rapidly degraded in a serum medium and its metabolites have no residual biological activity. It has been well established that the action of enzymes, namely that of dipeptidylaminopeptidase type IV, in a blood medium results in the hydrolysis of the peptide bond Ala$^2$-Asp$^3$ of GRF. This hydrolysis results in a multitude of negative consequences which were the subject of many studies reported in the literature. Essentially, this hydrolysis leads to the formation of truncated peptides of specific activity reduced to less than 1/1000 of the biological activity.

Clinical studies with children and adults have confirmed that natural hGRF (1-44)NH$_2$ or the active fragment hGRF (1-29)NH$_2$ are not potent enough to produce equal effects corresponding to those of recombinant GH.

It is well known that the anchoring of hydrophobic groups, such as —NEt$_2$ at the C-terminal of a peptidic sequence can result in a significantly increased specific activity. In terms of hydrophobicity, these results are contradicted by a fair number recent works such as those of Muranichi (S. Muranichi et al., 1991, *Pharm. Res.*, 8:649–652) which stress the inefficacy of the lauroyl group as a hydrophobic group at the N-terminal to create small peptide analogs having the desired biological activity. Hence, the contradictory investigations of the prior art failed to address the issue of finding a more potent GRF analog using hydrophobic residues.

Gaudreau et al. (P. Gaudreau et al., 1992, *J. Med. Chem.*, 35(10),: 1864–1869) describe the affinity of acetyl-, 6-aminohexanoyl-, and 8-aminooctanoyl-GRF(1-29)NH$_2$ with the rat pituitary receptor. In this report, none of the fatty acid-GRF compounds tested exhibited a higher affinity than hGRF(1-29)NH$_2$ itself, and the authors concluded that ". . . modifications to increase the hydrophobic character at the N-terminus of hGRF(1-29)NH$_2$ do not constitute a suitable approach to increase receptor affinity."

Coy et al. (D. H. Cow et al., 1987, *J. Med. Chem.*, 30:219–222) describe an acetyl-GRF peptide with an increased biological activity on a rat model, more particularly on a rat anesthetized with sodium pentobarbital. The in vitro GH response by cultured rat pituitary cells was also analyzed. However, these authors did not synthesize and test fatty acid-GRF analogs with a carbon chain longer than two (2) carbon atoms (acetyl group) added at the N-terminus region of the GRF and acetyl cannot be considered a hydrophobic group.

Up to now, most of the GRF analogs described (including those of Gaudreau et al. and those of Coy et al.) have been tested in rat models, either in vitro or in vivo. Since human and rat GRF(1-29)NH$_2$ are markedly different, the structure-activity relationships of GRF are different in both species. Therefore, it is not possible to extrapolate results obtained in rats to humans.

Accordingly, it is necessary to design GRF analogs with improved anabolic potency and having a prolonged activity. This increased potency could result from a resistance to serum degradation and/or from hyperagonistic properties.

It would be highly desirable to be provided with GRF analogs with increased anabolic potency.

SUMMARY OF THE INVENTION

One aim of the present invention is to provide new biodegradable GRF analogs with improved biological potency and prolonged activity.

Another aim of the present invention is to provide GRF analogs with increased anabolic potency and prolonged activity, i.e. capable to substantially elevate insulin-like growth factor I (IGF-I) levels when chronically administered in humans and animals.

Another aim of the present invention is to provide a means to render any GRF analog more biologically potent and with a prolonged activity.

Another aim of the present invention is to provide a method of producing active GRF analogs with improved anabolic potency and prolonged activity.

The present invention relates to the preparation of hydrophobic GRF analogs. These chimeric analogs include a hydrophobic moiety (tail), and can be prepared, either by anchoring one or several hydrophobic tails to the GRF, or by substituting one or several amino-acids by a pseudomicellar residue in the chemical synthesis of GRF. The GRF analogs in accordance with the present invention are characterized in that:

a) These analogs possess an enhanced biological activity; specifically, they are able to markedly increase GH and IGF-I blood levels when administered in an animal model closely related to human. This characteristic is particularly advantageous in that it results in a reduced dosage of an hyperactive compound being administered to the patient, thus improving treatment efficacy and reducing treatment costs.

b) Both natural amino acid and hydrophobic substances, such as fatty acids, are used for the chemical synthesis of the GRF analogs.

c) They present a high biological activity at infinitely small dosages.
d) They remain active for a prolonged period of time, with a high biological activity.

The use of fatty bodies in accordance with the present invention results in GRF analogs which overcome all the drawbacks of the prior art.

The GRF analogs of the present invention exhibit improved anabolic potency with a reduced dosage and have a prolonged activity. Furthermore, the present invention deals with GRF and any of its analogs, truncated or substituted.

In accordance with the present invention there is provided a hydrophobic GRF analog of formula A:

X—GRF-peptide     (A)

wherein;

the GRF peptide is a peptide of formula B;

A1-A2-Asp-Ala-Ile-Phe-Thr-A8-Ser-Tyr-Arg-Lys-A13-Leu-A15-Gln-Leu-A18-Ala-Arg-Lys-Leu-Leu-A24-A25-Ile-A27-A28-Arg-A30-$R_0$     (B)

wherein,
A1 is Tyr or His;
A2 is Val or Ala;
A8 is Asn or Ser;
A13 is Val or Ile;
A15 is Ala or Gly;
A18 is Ser or Tyr;
A24 is Gln or His;
A25 is Asp or Glu;
A27 is Met, Ile or Nle;
A28 is Ser or Asn;
A30 is a bond or any amino acid sequence of 1 up to 15 residues;
$R_0$ is $NH_2$ or $NH\text{-}(CH_2)n\text{-}CONH_2$, with n=1 to 12 and;
X is a hydrophobic tail anchored via an amide bond to the N-terminus of the peptide and said hydrophobic tail defining a backbone of 5 to 7 atoms;
wherein said backbone can be substituted by $C_{1-6}$ alkyl, $C_{3-6}$ cycloalkyl, or $C_{6-12}$ aryl;
and comprises at least one rigidifying moiety connected to at
least two atoms of the backbone;
said moiety selected from the group consisting of double bond, triple bond, saturated or unsaturated $C_{3-9}$ cycloalkyl, and $C_{6-12}$ aryl.

By the term rigidifying moiety is meant a moiety that will confer rigidity to the hydrophobic tail. The rigidifying moiety connects at least two atoms which are part of the backbone of the hydrophobic tail. For example, the backbone of the following hydrophic tail is as follows:

Tail                                     Backbone

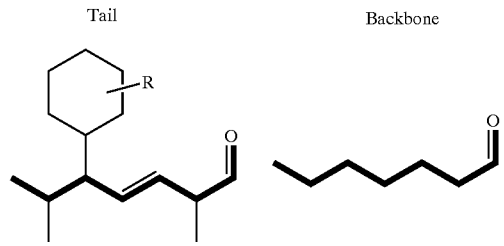

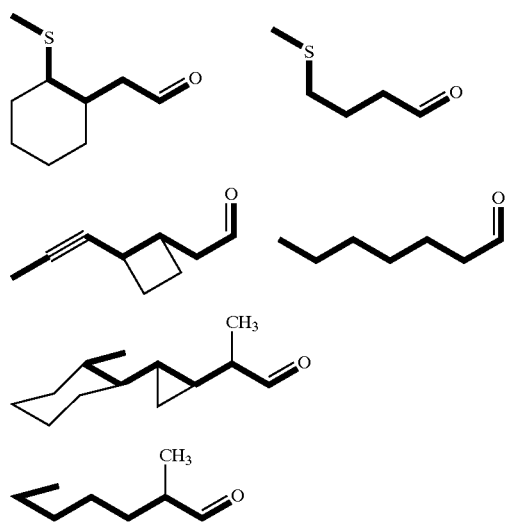

Preferably, the backbone is substituted with one rigidifying moiety selected from the group consisting of double bond, triple bond, saturated $C_{3-7}$ cycloalkyl and $C_6$ aryl.

Also preferably, the backbone is substituted with 2 rigidifying moieties which are independently selected from the group consisting of double bond and saturated or unsaturated $C_{3-9}$ cycloalkyl.

More preferably, the backbone is substituted with 2 rigidifying moieties which are independently selected from the group consisting of double bond, triple bond, saturated $C_{3-7}$ cycloalkyl and $C_6$ aryl.

In an alternative embodiment, the backbone is substituted one rigidifying moiety selected from the group consisting of double bond, triple bond, saturated $C_{3-7}$ cycloalkyl and $C_6$ aryl, which are located at the 3,4-positions, the 3,5-positions or the 3,6-positions of the backbone.

Preferably, the hydrophobic tail is selected from the group consisting of:

1

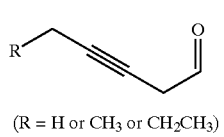

(R = H or $CH_3$ or $CH_2CH_3$)

2

(R = H or $CH_3$ or $CH_2CH_3$)
cis or trans, both as racemic mixtures
or pure enantiomeric pairs

3

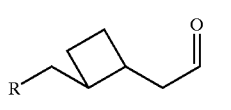

(R = H or $CH_3$ or $CH_2CH_3$)
cis or trans, both as racemic mixtures
or pure enantiomeric pairs -continued

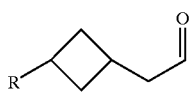

(R = H or CH₃ or CH₂CH₃)
cis or trans, (when R≠H)
both as racemic mixtures or pure
enantiomeric pairs

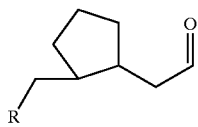

(R = H or CH₃ or CH₂CH₃)
cis or trans, both as racemic mixtures
or pure enantiomeric pairs.

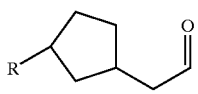

(R = H or CH₃ or CH₂CH₃)
cis or trans, (when R≠H) both as racemic
mixtures or pure enantiomeric pairs

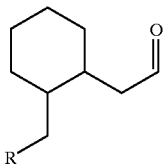

(R = H or CH₃ or CH₂CH₃)
cis or trans, both as racemic mixtures
or pure enantiomeric pairs.

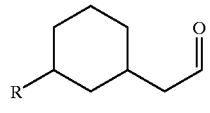

(R = H or CH₃ or CH₂CH₃)
cis or trans, (when R≠H) both as racemic
mixtures or pure enantiomeric pairs

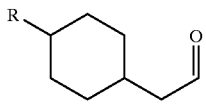

(R = H or CH₃)
cis or trans, (when R≠H) both as racemic
mixtures or pure enantiomeric pairs

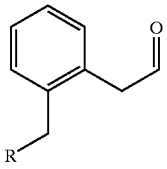

(R = H or CH₃ or CH₂CH₃)

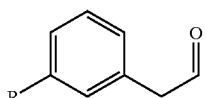

(R = H or CH₃ or CH₂CH₃)

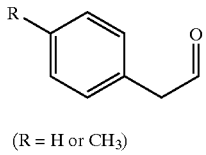

(R = H or CH₃)

In accordance with the present invention, there is provided a method of increasing the level of growth hormone in a patient which comprises administering to said patient an effective amount of a GRF analog of the present invention.

In accordance with the present invention, there is provided a method for the diagnosis of growth hormone deficiencies in patients, which comprises administering to said patient a GRF analog of the present invention and measuring the growth hormone response.

In accordance with the present invention, there is provided a method for the treatment of pituitary dwarfism or growth retardation in a patient, which comprises administering to said patient an effective amount of a GRF analog of the present invention.

In accordance with the present invention, there is provided a method for the treatment of wound or bone healing in a patient, which comprises administering to said patient an effective amount of a GRF analog of the present invention.

In accordance with the present invention, there is provided a method for the treatment of osteoporosis in a patient, which comprises administering to said patient an effective amount of a GRF analog of the present invention.

In accordance with the present invention, there is provided a method for improving protein anabolism (including protein sparing effect) in human or animal, which comprises administering to said human or animal an effective amount of a GRF analog of the present invention.

In accordance with the present invention, there is provided a method for inducing a lipolytic effect in human or animal afflicted with clinical obesity, which comprises administering to said human or animal an effective amount of a GRF analog of the present invention.

In accordance with the present invention, there is provided a method for the overall upgrading of somatotroph function in human or animal, which comprises administering to said human or animal an effective amount of a GRF analog of the present invention.

In the present invention the amino acids are identified by the conventional three-letter abbreviations as indicated below, which are as generally accepted in the peptide art as recommended by the IUPAC-IUB commission in biochemical nomenclature:

| | |
|---|---|
| Alanine | Ala |
| Arginine | Arg |
| Asparagine | Asn |

-continued

| | |
|---|---|
| Aspartic Acid | Asp |
| Cysteine | Cys |
| Glutamic Acid | Glu |
| Glycine | Gly |
| Histidine | His |
| Leucine | Leu |
| Lysine | Lys |
| Methionine | Met |
| Ornithine | Orn |
| Phenylalanine | Phe |
| Proline | Pro |
| Serine | Ser |
| Threonine | Thr |
| Tryptophane | Trp |
| Tyrosine | Tyr |
| D-Tyrosine | Tyr |
| Valine | Val |

The term "natural amino acid" means an amino acid which occurs in nature or which is incorporated as an amino acid residue in a naturally occurring peptide. In addition, the abbreviation Nle is intended to mean Norleucine.

| | |
|---|---|
| TFA | Trifluoroacetic acid; |
| HOBt | 1-Hydroxybenzotriazole; |
| DIC | Diisopropylcarbodiimide; |
| DMF | Dimethylformamide; |
| Pip | Piperidine; |
| DMAP | 4-dimethylaminopyridine; |
| Boc | t-butyloxycarbonyl; |
| Fmoc | Fluorenylmethyloxycarbonyl; |
| BOP | Benzotriazo-1-yloxytris (dimethylamino) phosphonium hexafluorophosphate; |
| Me | Methyl; |
| HF | Hydrofluoric acid; |
| NEt$_3$ | Triethylamine; and |
| TEAP | Triethylammonium phosphate (buffer). |

All the peptide sequences set out herein are written according to the generally accepted convention whereby the N-terminal amino acid is on the left and the C-terminal amino acid is on the right.

BRIEF DESCRIPTION OF THE DRAWINGS

FIG. 6A to 6C illustrate examples of specific synthesis of the X-portion of GRF analogs with preferred radicals R in accordance with the present invention; and FIG. 7A and 7B illustrate the effect of 8 different hGRF (1-44)NH$_2$ analogs of the present invention on IGF-1 levels in pigs.

DETAILED DESCRIPTION OF THE INVENTION

Figure 1:
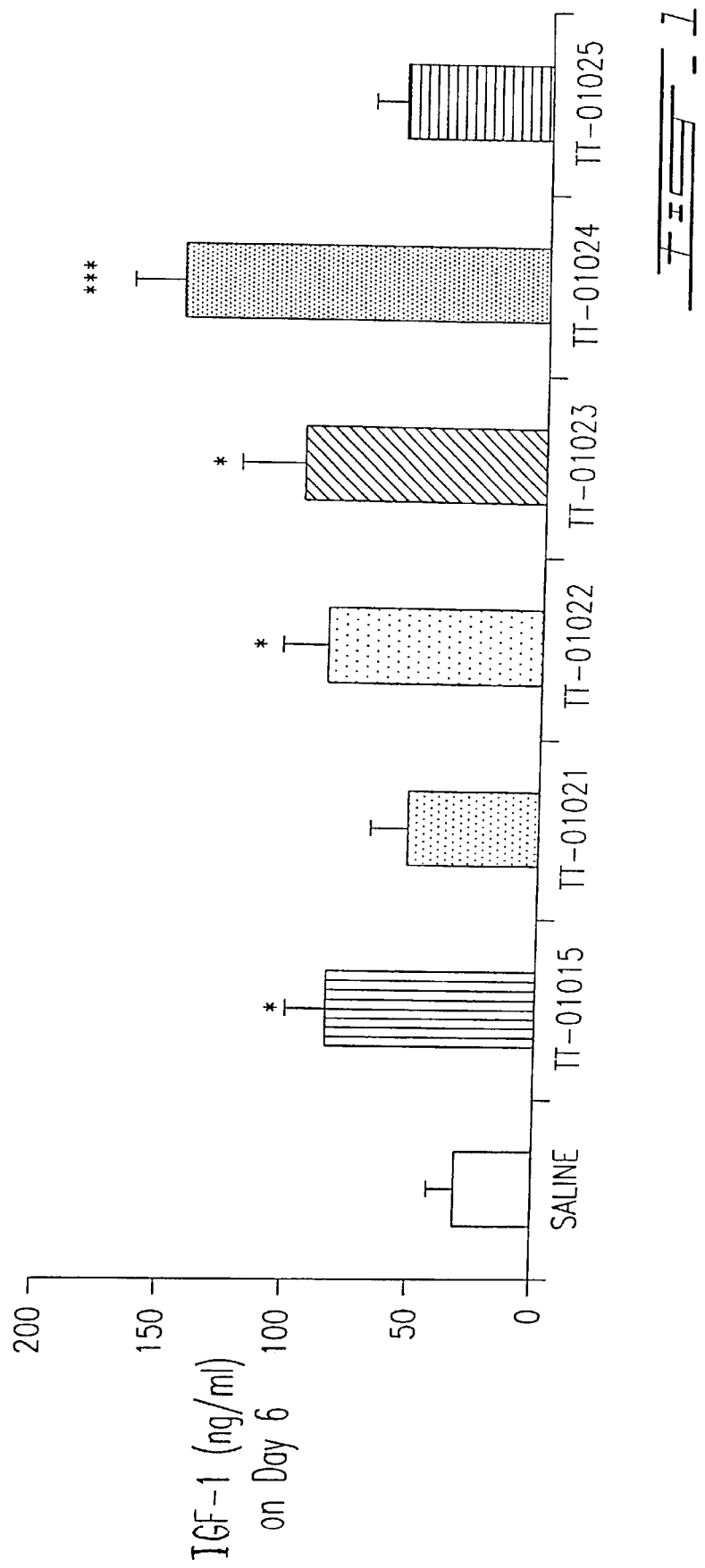
FIG. 1 is a graph of the effect of subcutaneously injected hGRF(1-29)NH$_2$ analogs on pig serum IGF-1.

The present invention relates to the use of fatty bodies, namely pseudomicellar residues and/or hydrophobic tails, to produce a new family of highly potent, chimeric fatty body-GRF analogs.

In accordance with the present invention, the fatty body-GRF analogs can be chemically synthesized by anchoring one or several hydrophobic tails at the N- terminal portion of GRF or one of its analogs.

For a better carrying out of the chemical anchoring reaction, hydrophobic functionalized under the acid form are preferably used. In these conditions, the anchoring reaction is preferably effected in a solid phase (Merrifield R. B., 1963, J. Am. Chem. Soc., 85:2149; 1964, J. Am. Chem. Soc., 86:304) using extremely active reagents such as for example Benzotriazole-1-yloxytris (dimethylamino) phosphonium hexafluorophosphate known in the prior art (B. Castro et al., 1975, Tetrahedron letters, Vol. 14:1219).

In the case where the hydrophobic tail to be anchored consists in a fatty acid, the activation in view of the anchoring may be carried out in situ. Depending on the synthesis strategies used, the peptide anchoring site is liberated just prior to the anchoring in traditional deprotection conditions (Gross et Meienhofer, 1981, The peptides, vol. 3, Academic press: pages 1–341). The hydrophobic tail (Ht) is then condensed with the anchoring agent in organic solvents such as an ether (tetrahydrofuranne), an aliphatic halogenated solvent (dichloromethane), a nitrile (acetonitrile) or an amide (dimethylformamide).

With respect to the anchoring dynamic, the preferred working temperatures are between 20 and 60° C. The anchoring reaction time when hydrophobic tail used are more and more hydrophobic, varies inversely with temperature, but varies between 0.1 and 24 hours.

As an illustrative example, the triacyl lysine synthesis as set forth below illustrates in a schematic manner the whole of the anchoring principle of a hydrophobic fatty acid tail.

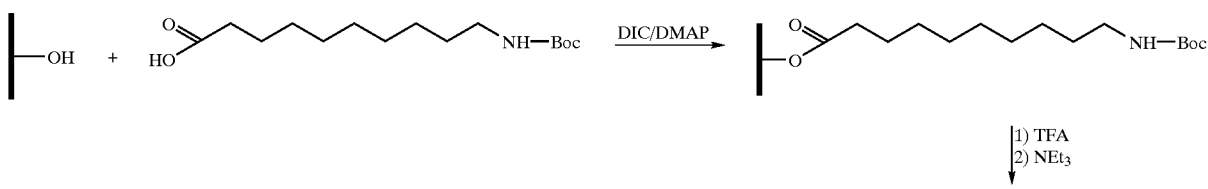

-continued

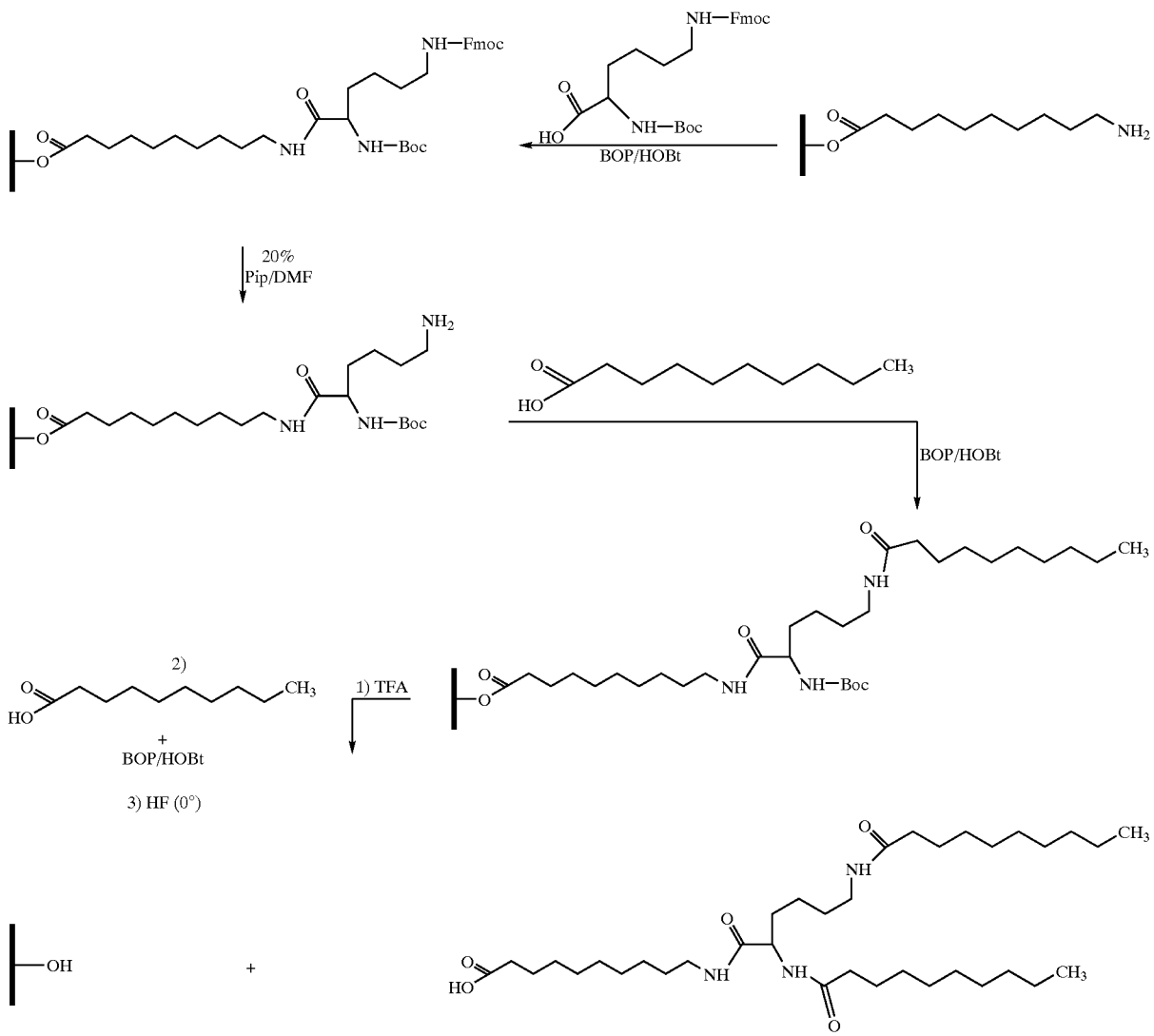

General GRF analogs synthesis steps were carried out by solid-phase methodology on a 9050™ plus peptide synthesizer (Millipore Corporation, Milford, Mass.) using Fmoc strategy and synthesis cycles supplied by Millipore. Fmoc amino acids were supplied by Bachem California and other commercials sources. Sequential Fmoc chemistry using BOP/HOBt as coupling methodology were applied to the starting Fmoc-Pal-PEG resin (Millipore, catalog number: GEN 913383) for the production of C-terminal carboxamides. Fmoc deprotections were accomplished with piperidine 20% solution in DMF. After synthesis completion, the resin was well washed with DMF and ether prior to drying. Final cleavages of side chain protecting groups and peptide-resin bonds were performed using Millipore supplied procedure consisting of the following mixture: TFA, water, phenol, triisopropylsilane (88:5:5:2). Peptides were then precipitated and washed with ether prior to drying. Reverse phase HPLC purification (buffer A: TEAP 2.5; buffer B: 80% $CH_3CN$ in A) using a waters prep 4000, absorbance 214 nm, detector model 486, flow rate 50 ml/min.; linear gradient generally from 25 to 60% B in 105 min.) followed by a desalting step (buffer C:0.1% TFA in $H_2O$; buffer D:0.1% TFA in $CH_3CH/H_2O$ 80:20) afforded peptides in yields amounting from 10 to 30% with homogeneity greater than 97% as estimated by HPLC (millennium/photodiode array detection).

In accordance with the present invention, the pig was selected as a test specie, since it is a valuable preclinical model for the development of GRF analogs. Indeed, human and porcine GRF(1-29)$NH_2$ share a 100% homology of structure, and the physiological pattern of GH secretion is almost identical in both species.

Moreover, the potency of the GRF analogs was assessed as their ability to significantly increase IGF-I blood levels rather than their acute GH releasing potency. Indeed, it is known that the anabolic and healing effects of GH or GRF induced GH are mediated by an increase in IGF-I synthesis and secretion. Therefore, the measurement of GRF induced IGF-I elevation is the best indicator of the treatment efficacy.

The present invention will be more readily understood by referring to the following examples which are given to illustrate the invention rather than to limit its scope.

EXAMPLE I

Effect of Repeated Administrations of [BUTYRYL⁰], [OCTANOYL⁰]-, [HEXANOYL⁰]-[HEXANOYL³⁰], [HEXANOYL⁰,³⁰], HGRF(1-29)NH₂ and [HEXANOYL⁰]HGRF(1-44)NH₂ VS hGRF(1-29)NH₂ on Serum IGF-I Levels in Pigs The objective of these experiments was to assess the potential of the GRF analogs as anabolic agents. It is known that GH or GRF-induced GH secretion exert their anabolic effect via an increase in insulin-like growth factor I (IGF-I) synthesis and secretion, that result in elevated levels of circulating IGF-I. It has been previously demonstrated that the intensity of the anabolic response to a GRF analog treatment is proportional to the increase in IGF-I levels in pigs (Dubreuil P. et al., 1990, *J. Anim. Sci.*, 68:1254–1268).

Therefore, in order to investigate the anabolic potency of the fatty acid-GRF analogs, their ability to increase IGF-I levels following repeated S.C. administrations in pig was evaluated.

Experiment 1

26 Landrace x Yorkshire castrated male pigs (40–45 kg BW) were randomly distributed into 4 experimental groups:
1—hGRF(1-29)NH₂ (20 µg/kg, n=7)
2—[octanoyl⁰] hGRF(1-29)NH₂ (20 µg/kg, n=6)
3—[hexanoyl⁰] hGRF(1-29)NH₂ (20µg/kg, n=6)
4—[butyryl⁰] hGRF(1-29)NH₂ (20 µg/kg, n=7)

Each animal was injected BID (twice a day) subcutaneously for 4 consecutive days. One blood sample was collected each morning prior to the first injection of the day, and the day after the last injection, for IGF-I measurement.

Experiment 2

40 Landrace x Yorkshire castrated male pigs (40–45 kg BW) were randomly distributed into 5 experimental groups:
1—saline (n=8)
2—hGRF(1-29)NH₂ (40 µg/kg, n=8)
3—[hexanoyl⁰] hGRF(1-29)NH₂ (10 µg/kg, n=8)
4—[hexanoyl⁰] hGRF(1-29)NH₂ (20 µg/kg, n=8)
5—[hexanoyl⁰] hGRF(1-29)NH₂ (40 µg/kg, n=8)

Each animal was injected BID (twice a day) subcutaneously for 5 consecutive days. One blood sample was collected each morning prior to the first injection of the day, and the day after the last injection, for IGF-I measurement.

Experiment 3

48 Landrace x Yorkshire castrated male pigs (40–45 kg BW) were randomly distributed into 6 experimental groups:
1—Saline (n=8)
2—hGRF(1-44)NH₂ (30 µg/kg, n=8)
3—[hexanoyl⁰]hGRF(1-44)NH₂ (30 µg/kg, n=8)
4—[hexanoyl⁰]hGRF(1-29)NH₂ (20 µg/kg, n=8)
5—[hexanoyl³⁰]hGRF(1-29)NH₂ (20 µg/kg, n=8)
6—[hexanoyl⁰,³⁰]hGRF(1-29)NH₂ (20 µg/kg, n=8)

The selected doses were 30 µg/kg for hGRF(1-44)NH₂ analogs and 20 µg/kg for hGRF(1-29)NH₂ analogs, which give identical doses on a molar basis. Each animal was injected BID (twice a day) subcutaneously for 5 consecutive days. One blood sample was collected each morning prior to the first injection of the day, and the day after the last injection, for IGF-I measurements.

IGF-I Measurements

IGF-I levels were measured in pig serum by double antibody radioimmunoassay after formic acid-acetone extraction, as previously described (Abribat T. et al., 1993, *J. Endocrinol.*, 39:583–589). The extraction prior to radioimmunoassay is a necessary step to remove endogenous IGF-binding proteins.

Statistical Analysis

In both experiments, the IGF-I data were analyzed by a two way repeated measure analysis of variance, with day and treatment (GRF analog) as sources of variation. Multiple comparison procedures were there run (Student-Newman Keuls method). A P<0.05 was considered as statistically significant.

Results

Experiment 1

There were both a significant effect of day (P=0.0004) and a significant treatment x day interaction (P=0.011), indicating that the increase in IGF-I levels was dependent on the analog tested (Table 1). Blood samples for IGF-I measurements were collected daily prior to the first injection of compounds. Data are shown as mean±SEM of 6 to 7 values per group.

TABLE 1

Effect of repeated SC injection (20 µg/kg BID x 4 days) of GRF analogs on serum IGF-I levels

| Treatment (BID, 20 µg/kg SC) | Day 1 (pretreatment) (ng/ml) | Day 2 (ng/ml) | Day 3 (ng/ml) | Day 4 (ng/ml) | Day 5 (ng/ml) |
| --- | --- | --- | --- | --- | --- |
| hGRF(1–29)NH₂ | 252 ± 28 | 235 ± 19 | 263 ± 16 | 258 ± 17 | 262 ± 24 |
| [octanoyl⁰] hGRF (1–29)NH₂ | 316 ± 22 | 287 ± 20 | 301 ± 37 | 301 ± 37 | 318 ± 39 |
| [hexanoyl⁰] hGRF (1–29)NH₂ | 248 ± 20 | 281 ± 28 | 299 ± 26 | 319 ± 22[a] | 342 ± 21[a,b] |
| [butyryl⁰] hGRF (1–29)NH₂ | 278 ± 20 | 281 ± 24 | 302 ± 26 | 289 ± 26 | 293 ± 23 |

Treatment P = 0.42
Day P = 0.0004
Treatment x Day P = 0.011
[a]P < 0.05 when compared to day 1
[b]P < 0.05 when compared to day 2

Multiple comparisons revealed that only [hexanoyl⁰] hGRF(1-29)NH₂ elicited an increase in IGF-I levels, which was significant on days 4 (29%, P<0.05) and 5 (38%, P<0.05). Human GRF(1-29)NH₂ had no effect on IGF-I levels at the dose tested.

Experiment 2

There were both a significant effect of day (P<0.0001) and a significant treatment x day interaction (P<0.0001), indicating that the increase in IGF-I levels was dependent on the analog tested (Table 2). Blood samples for IGF-I measurements were collected daily prior to the first injection of the day. Data are shown as mean±SEM of 8 values per group.

TABLE 2

Dose-related effect of repeated SC injection (BID × 5 days) of GRF analogs on serum IGF-I levels

| Treatment BID, SC | Day 1 (pretreatment) (ng/ml) | Day 2 (ng/ml) | Day 3 (ng/ml) | Day 4 (ng/ml) | Day 5 (ng/ml) | Day 6 (ng/ml) |
|---|---|---|---|---|---|---|
| saline | 282 ± 33 | 266 ± 30 | 281 ± 34 | 293 ± 30 | 287 ± 32 | 289 ± 33 |
| hGRF(1-29)NH$_2$ (40 μg/kg) | 244 ± 24 | 243 ± 16 | 267 ± 20 | 275 ± 27 | 267 ± 17 | 256 ± 15 |
| [hexanoyl$^0$] hGRF (1-29)NH$_2$ (10 μg/kg) | 303 ± 31 | 327 ± 20 | 337 ± 25 | 338 ± 25 | 366 ± 37$^a$ | 350 ± 34$^a$ |
| [hexanoyl$^0$] hGRF (1-29)NH$_2$ (20 μg/kg) | 302 ± 38 | 341 ± 37 | 368 ± 43$^a$ | 362 ± 40$^a$ | 362 ± 45$^a$ | 368 ± 57$^a$ |
| [hexanoyl$^0$] hGRF (1-29)NH$_2$ (40 μg/kg) | 252 ± 35 | 275 ± 32 | 319 ± 31$^a$ | 354 ± 41$^{a,b}$ | 350 ± 34$^{a,b}$ | 374 ± 33$^{a,b,c}$ |

Treatment P = 0.23; Day P = 0.0001
Treatment × Day P = 0.0001
$^a$P < 0.05 when compared to day 1
$^b$P < 0.05 when compared to day 2
$^c$P < 0.05 when compared to day 3

Multiple comparisons revealed that all three tested doses of [hexanoyl$^0$] hGRF(1-29)NH$_2$ increased IGF-I levels. At 10 μg/kg, IGF-I levels were significantly increased at days 5 and 6 (16 to 21%, P<0.05). At 20 μg/kg, they were increased at days 3, 4, 5 and 6 (20 to 22%, P<0.05). At 40 μg/kg, they were increased at days 3, 4, 5 and 6 (27 to 48%, P<0.05). The serum IGF-I levels remained stable in saline— and hGRF(1-29)NH$_2$—treated pigs.

Finally, a regression analysis revealed that the increase in IGF-I concentrations from day 1 to day 6 was dependent on the dose of [hexanoyl$^0$] hGRF(1-29)NH$_2$ (ΔIGF-I=11.9+ (2.77 * dose); r=0.68, P<0.0001).

Experiment 3

There were both a significant effect of day (P<0.0001) and a significant treatment × day interaction (P<0.0001), indicating that the increase in IGF-I levels was dependent on the analog tested (Table IV). Multiple comparison revealed that analogs with an hexanoyl function branched at the N-terminal region of GRF were highly potent:

[hexanoyl$^0$] hGRF(1-29)NH$_2$ significantly increased IGF-I levels on days 5 and 6 (by 28% and 31%, P<0.05)

[hexanoyl$^{0, 30}$] hGRF(1-29)NH$_2$ significantly increased IGF-I levels on days 4, 5 and 6 (by 32%, 35% and 43%, P<0.05)

[hexanoyl$^0$] hGRF(1-44)NH$_2$ significantly increased IGF-I levels on days 3, 4, 5 and 6 (by 41%, 54%, 50% and 61%, P<0.05)

As previously observed for hGRF(1-29)NH$_2$ (experiments 1 and 2), the full length hGRF(1-44)NH$_2$ had little or no effect on IGF-I levels (except for a significant effect on day 5, which was not sustained on day 6). Finally, the anchoring of an hexanoyl function at the C-terminal region of hGRF(1-29)NH$_2$ yielded an analog with increased potency when compared to hGRF(1-29)NH$_2$ (21% increased in IGF-I levels on day 6, P<0.05), but less potent than [hexanoyl$^0$]hGRF(1-29)NH$_2$.

Human GRF(1-29)NH$_2$ and hGRF(1-44)NH$_2$ were injected at 20 μg/kg and 30 μg/kg, respectively, in order to achieve equimolar concentrations. Data shown are mean±SEM of 8 values per group.

TABLE 3

Effect of multiple SC injections of GRF analogs (BID × 5 days) on serum IGF-I levels in growing pigs

| Treatment BID, SC | Day 1 (pretreatment) (ng/ml) | Day 2 (ng/ml) | Day 3 (ng/ml) | Day 4 (ng/ml) | Day 5 (ng/ml) | Day 6 (ng/ml) |
|---|---|---|---|---|---|---|
| saline | 215 ± 21 | 215 ± 28 | 219 ± 25 | 226 ± 28 | 249 ± 30 | 234 ± 24 |
| hGRF(1-44)NH$_2$ (30 μg/kg) | 245 ± 21 | 254 ± 22 | 285 ± 26 | 297 ± 28 | 303 ± 26$^a$ | 296 ± 26 |
| [hexanoyl$^0$] hGRF (1-29)NH$_2$ (20 μg/kg) | 272 ± 45 | 292 ± 52 | 292 ± 57 | 315 ± 57 | 347 ± 44$^{a,b,c}$ | 356 ± 44$^{a,b,c}$ |
| [hexanoyl$^{30}$] hGRF (1-29)NH$_2$ (20 μg/kg) | 297 ± 30 | 270 ± 25 | 287 ± 24 | 278 ± 18 | 276 ± 20 | 327 ± 24$^b$ |
| [hexanoyl$^{0,30}$] hGRF (1-29)NH$_2$ (20 μg/kg) | 205 ± 24 | 212 ± 26 | 253 ± 33 | 271 ± 36$^{a,b}$ | 277 ± 29$^{a,b}$ | 294 ± 26$^{a,b}$ |

TABLE 3-continued

Effect of multiple SC injections of GRF analogs (BID × 5 days) on serum IGF-I levels in growing pigs

| Treatment BID, SC | Day 1 (pretreatment) (ng/ml) | Day 2 (ng/ml) | Day 3 (ng/ml) | Day 4 (ng/ml) | Day 5 (ng/ml) | Day 6 (ng/ml) |
|---|---|---|---|---|---|---|
| [hexanoyl$^0$] hGRF (1–44)NH$_2$ (30 μg/kg) | 241 ± 30 | 290 ± 33 | 340 ± 41$^a$ | 372 ± 40$^{a,b}$ | 361 ± 46$^{a,b}$ | 388 ± 49$^{a,b,c}$ |

Treatment P = 0.16
Day P < 0.0001
Treatment × Day P < 0.0001
$^a$P < 0.05 when compared to day 1
$^b$P < 0.05 when compared to day 2
$^c$P < 0.05 when compared to day 3

Conclusions

Neither hGRF(1-29)NH$_2$ nor hGRF(1-44)NH$_2$ at doses ranging is from 20 to 40 μg/kg were able to modulate IGF-I levels. However, the anchoring of fatty acid rendered GRF more potent and yielded analogs with markedly improved activity on IGF-I secretion. The anchoring of fatty acids was efficient in improving the anabolic potency of both hGRF (1-29)NH$_2$ and hGRF(1-44)NH$_2$. From the above results, it is concluded that the ideal fatty acid to use is hexanoic acid or any C6 fatty derivative, and that it should be preferably anchored at the N-terminal region of GRF to yield maximally potent analogs.

EXAMPLE II

Comparative Effects of GRF Analogs on IGF-I Levels in Pigs

This was a 5-day treatment, twice a day S.C. administration of one single dose of each test article vs saline. This experiment was conducted to compare the efficacy of (Aminohexanoyl)0 hGRF (1-29) NH$_2$, (Hexylformiate)$_0$ hGRF (1-29) NH$_2$, (Hexenoyl trans-2)$_0$ hGRF (1-29) NH$_2$, (Hexenoyl trans-3)$_0$ hGRF (1-29) NH$_2$ and (Muconoyl)$_0$ hGRF (1-29) NH$_2$ to that of(Hexanoyl)$_0$ hGRF (1-29) NH$_2$.

All tested compounds belong to the same family of GRF analogs: they are a combination of the natural GRF and natural fatty acids, designed to improve the activity of the molecule.

| Identity of tested analogs: | | in saline |
|---|---|---|
| TT-01015 | (Hexanoyl)$_0$ hGRF (1–29) NH$_2$ | 20 μg/kg |
| TT-01021 | (Aminohexanoyl)$_0$ hGRF (1–29) NH$_2$ | 20 μg/kg |
| TT-01022 | (Hexylformiate)$_0$ hGRF (1–29) NH$_2$ | 20 μg/kg |
| TT-01023 | (Hexenoyl trans-2)$_0$ hGRF (1–29) NH$_2$ | 20 μg/kg |
| TT-01024 | (Hexenoyl trans-3)$_0$ hGRF (1–29) NH$_2$ | 20 μg/kg |
| TT-01025 | (Muconoyl)$_0$ hGRF (1–29) NH$_2$ | 20 μg/kg |

Route and Frequency of Test Article

ADMINISTRATION: Two daily subcutaneous injections.
TEST SYSTEM: Landrace × Yorkshire pigs.
ANIMAL DESCRIPTION: Fifty six (56) growing barrows pigs weighing 35 kg at the time of purchase.
RATION: Commercial feed concentrate (18% protein) offered ad libitum.

EXPERIMENTAL

DESIGN: Fifty six (56) pigs were randomly distributed into 7 experimental groups (n=8 pigs per group). Each group received two daily S.C. administration of the following treatments (volume: 3 ml, S.C. injection).

group 1: saline 2×/day
group 2: TT-01015 20 μg/kg 2×/day
group 3: TT-01021 20 μg/kg 2×/day
group 4: TT-01022 20 μg/kg 2×/day
group 5: TT-01023 20 μg/kg 2×/day
group 6: TT-01024 20 μg/kg 2×/day
group 7: TT-01025 20 μg/kg 2×/day Treatments were administered from day 1 to 5. Immediately before the injections, one blood sample were collected from each animal, and additional blood samples were collected on day 6.

Blood samples were allowed to clot, serum was harvested by centrifugation and submitted to IGF-I assays.

Results are shown in FIG. 1 as D-IGF-I, which is defined as the increase in IGF-I levels from day 1 (pretreatment levels) to day 6 (after 5 days of GRFs administrations). Among all analog tested, only hexanoyl-, hexylformiate-, hexenoyl trans2- and hexenoyl trans3-hGRF(1-29)NH$_2$ significantly increased IGF-I levels over the 6-day study period, whereas aminohexanoyl- and muconoyl-hGRF(1-29)NH$_2$ did not. Since hGRF(1-29)NH$_2$ has been shown to be ineffective at the same dose in the same conditions in previous assays (see Example I), these results show that the addition of various C6 carbon chains at the N-terminus region of GRF increases its bioactivity.

EXAMPLE III

Intravenous GH-releasing Potency of (Hexenoyl trans-3)$_0$ hGRF (1-29) NH$_2$ vs hGRF(1-29)NH$_2$ in Pigs This experiment was conducted to test the I.V. acute GH-releasing potency of (Hexenoyl trans-3)$_0$ hGRF (1-29) NH$_2$, a GRF analog, in a model physiologically close to human and to compare it to that of hGRF(1-29)NH$_2$.

(Hexenoyl trans-3)$_0$ hGRF (1-29) NH$_2$ is a combination of the natural hGRF(1-29)NH$_2$ and natural fatty acids. This study was a multidose, single I.V. injection study.

| | | |
|---|---|---|
| TT-01024 | (Hexenoyl trans-3)₀ hGRF (1–29) NH₂ | 0.25 μg/kg |
| TT-01024 | (Hexenoyl trans-3)₀ hGRF (1–29) NH₂ | 1 μg/kg |
| TT-01024 | (Hexenoyl trans-3)₀ hGRF (1–29) NH₂ | 4 μg/kg |
| hGRF(1–29)NH₂ | | 0.25 μg/kg |
| hGRF(1–29)NH₂ | | 1 μg/kg |
| hGRF(1–29)NH₂ | | 4 μg/kg |

Route and frequency of test article

ADMINISTRATION: intravenous acute injection.
TEST SYSTEM: Landrace x Yorkshire pigs.
ANIMAL DESCRIPTION: Fifty six (56) growing barrows pigs weighing 35 kg at the time of purchase.
RATION: Commercial feed concentrate (18% protein) offered ad libitum.
EXPERIMENTAL
DESIGN: Fifty (56) pigs (4 spare animals) were cannulated (a catheter surgically implanted in one jugular vein) within on week, before the study. On days 1 and 7, cannulated animals were randomly distributed into 7 groups (n=4 pigs per group).

| | |
|---|---|
| group 1: saline | |
| group 2: TT-01024 | 0.25 μg/kg |
| group 3: TT-01024 | 1 μg/kg |
| group 4: TT-01024 | 4 μg/kg |
| group 5: hGRF(1–29)NH₂ | 0.25 μg/kg |
| group 6: hGRF(1–29)NH₂ | 1 μg/kg |
| group 7: hGRF(1–29)NH₂ | 4 μg/kg |

Blood samples for pGH assay were collected every 20 min from 1 hour before to 5 hours after GRF injections, with additional samplings 10 and 30 min after injection (n=21 samples). Blood samples are allowed to clot at +4° C. Serum will be harvested by centrifugation, stored at −20° C. and submitted to pGH assays.

Figure 2:
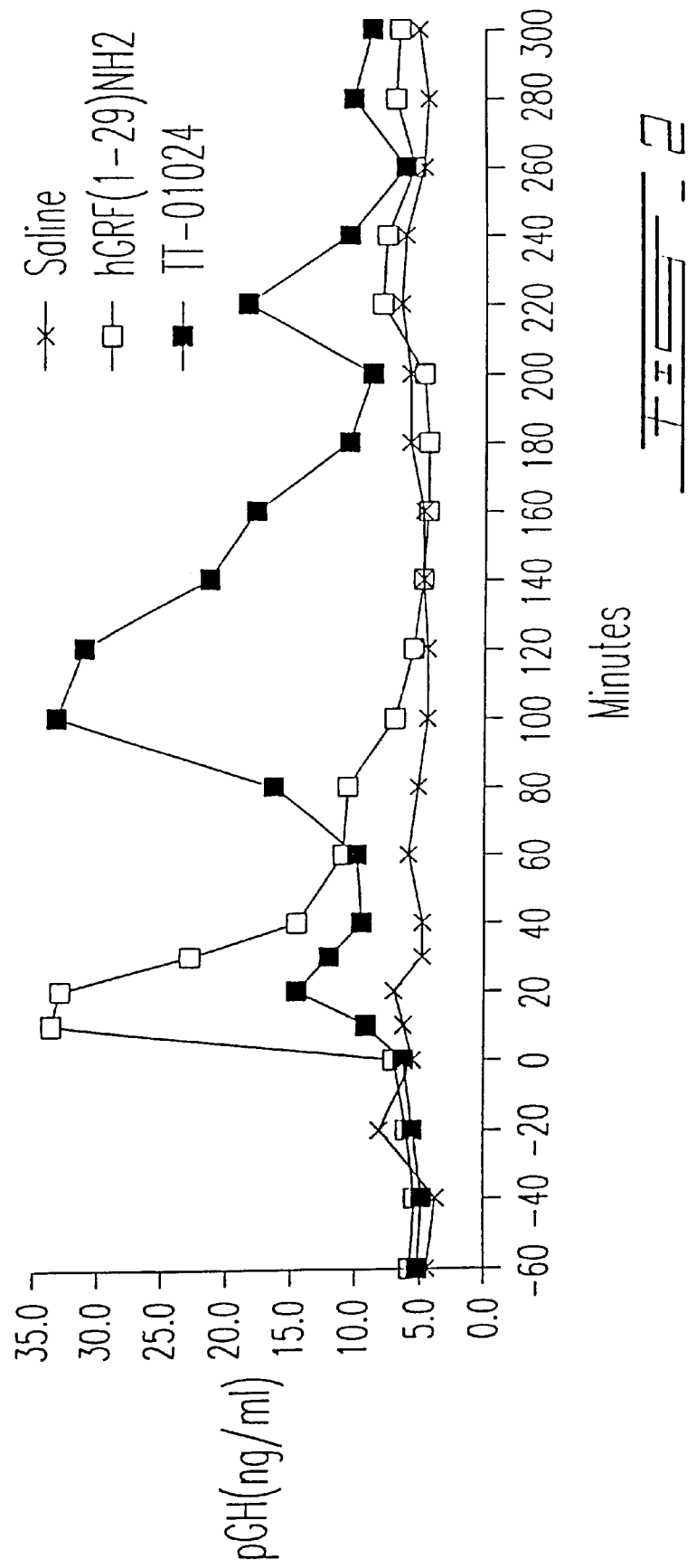
FIG. 2 is a curve of the effect of one intravenous injection of (4 μg/kg) hGRF(1-29)NH$_2$ and (4 μg/kg) (Hexenoyl trans-3)° hGRF (1-29)NH$_2$ (TT-01024)+analog on pig serum GH.
Figure 3:
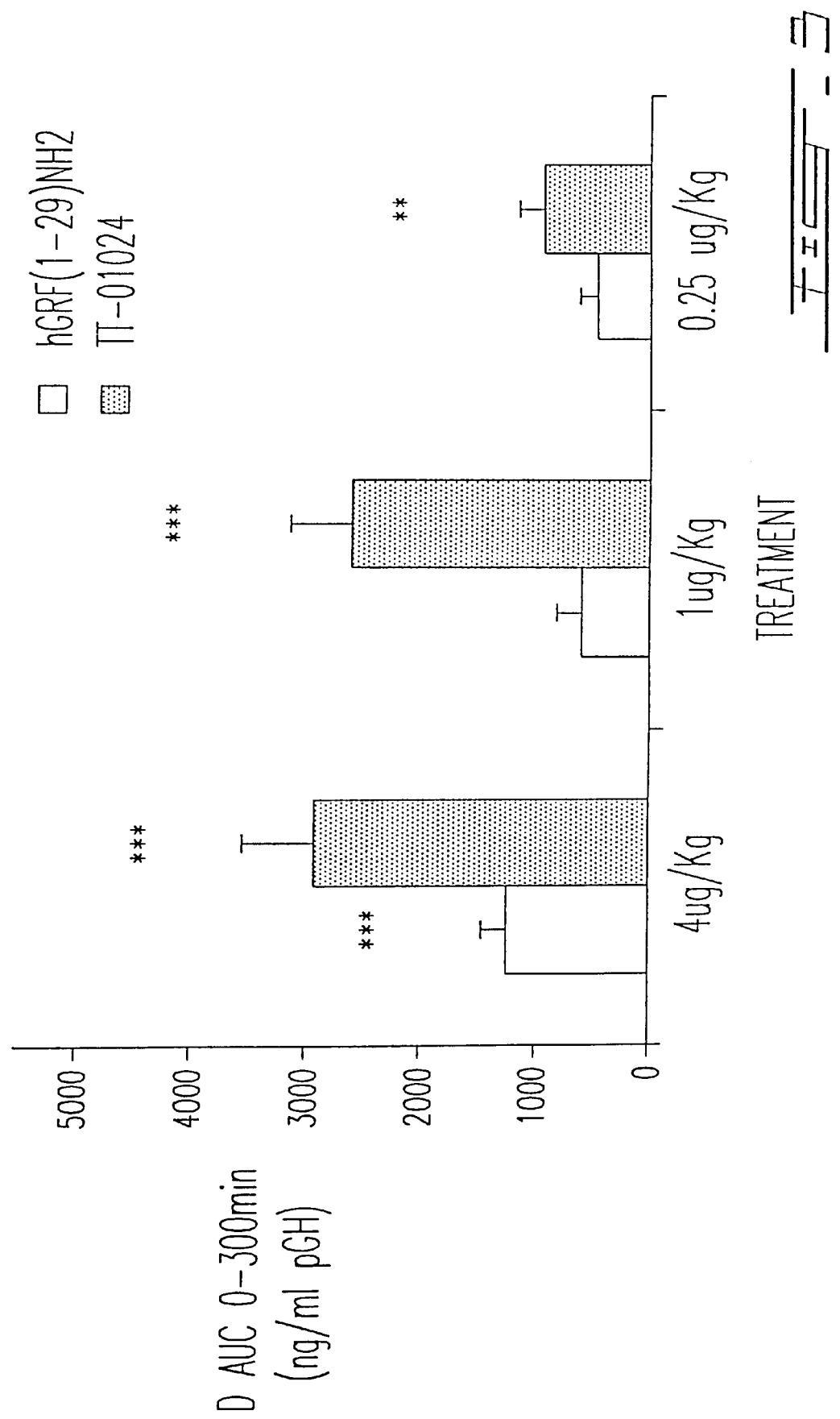
FIG. 3 is a graph showing the effect of various doses of hGRF(1-29)NH$_2$ vs [hexenoyl trans-3]° hGRF(1-29)NH$_2$ (TT-01024) on the GH area under the curve over 300 minutes following I.V. administration (P<0.01 and *P<0.001 when compared to the basal period —60 to 0 min–)

Results are illustrated in FIGS. 2 and 3. As shown in FIG. 2, hGRF(1-29)NH₂ (4 μg/kg) induced a rapid GH release that was sustained for approximately 60 minutes following injection. In contrast, hexenoyl trans3-hGRF(1-29)NIH2 injected at the same dose increased GH levels over a longer period, approximately 260 minutes. In addition, the GH response in the first 60 minutes was moderate, suggesting that this analog acts as a GRF, being processed in serum into native GRF in the minutes or hours following injection. As shown in FIG. 3, which presents the effects of various doses of GRF and the analog on the GH area under the curve (0 to 300 minutes following injection), hGRF(1-29)NH₂ produced a significant effect on GH secretion at 4pg/kg, but not at 0.25 or 1 μg/kg, whereas hexenoyl trans3-hGRF(1-29)NH₂ elicited a significant response at all 3 doses tested. In conclusion, these results show that hexenoyl trans3-hGRF (1-29)NH₂ is a GRF analog with increased potency on GH secretion, and suggest that it may act as a GRF, being protected from enzymatic degradation in serum.

EXAMPLE IV

Subcutaneous GH-releasing Potency of (Hexenoyl trans-3)₀ hGRF (1-29) NH₂ vs hGRF(1-29)NH₂ in Pigs This experiment was conducted to test the S.C. acute GH-releasing potency of (Hexenoyl trans-3)0 hGRF (1-29) NH₂, a GRF analog, in a model physiologically close to human and to compare it to that of hGRF(1-29)NH₂.

| | | |
|---|---|---|
| TT-01024 | (Hexenoyl trans-3)₀ hGRF (1–29) NH₂ | 0.31 μg/kg |
| TT-01024 | (Hexenoyl trans-3)₀ hGRF (1–29) NH₂ | 1.25 μg/kg |
| TT-01024 | (Hexenoyl trans-3)₀ hGRF (1–29) NH₂ | 5 μg/kg |
| TT-01024 | (Hexenoyl trans-3)₀ hGRF (1–29) NH₂ | 20 μg/kg |
| hGRF(1–29)NH₂ | | 1.25 μg/kg |
| hGRF(1–29)NH₂ | | 5 μg/kg |
| hGRF(1–29)NH₂ | | 20 μg/kg |

Route and Frequency of Test Article

ADMINISTRATION: Subcutaneous acute injection.
TEST SYSTEM: Landrace x Yorkshire pigs.
ANIMAL DESCRIPTION: Sixty four (64) growing barrows pigs weighing 35 kg at the time of purchase.
RATION: Commercial feed concentrate (18% protein) offered ad libitum.
EXPERIMENTAL
DESIGN: Thirty six (36) pigs (4 spare animals) were cannulated (a catheter surgically implanted in one jugular vein) within one week, before the study. On days 1 and 7, cannulated animals were randomly distributed into 8 groups (n=4 pigs per group).

| | |
|---|---|
| group 1: saline | |
| group 2: TT-01024 | 0.31 μg/kg |
| group 3: TT-01024 | 1.25 μg/kg |
| group 4: TT-01024 | 5 μg/kg |
| group 5: TT-01024 | 20 μg/kg |
| group 6: hGRP(1–29)NH₂ | 1.25 μg/kg |
| group 7: hGRF(1–29)NH₂ | 5 μg/kg |
| group 8: hGRF(1–29)NH₂ | 20 μg/kg |

Blood samples for pGH assay were collected every 20 min from 1 hour before to 7 hours after GRF injections, (n=25 samples). Blood samples were allowed to clot at +4CC. Serum is harvested by centrifugation, stored at −20° C. and submitted to pGH assays.

Figure 4:
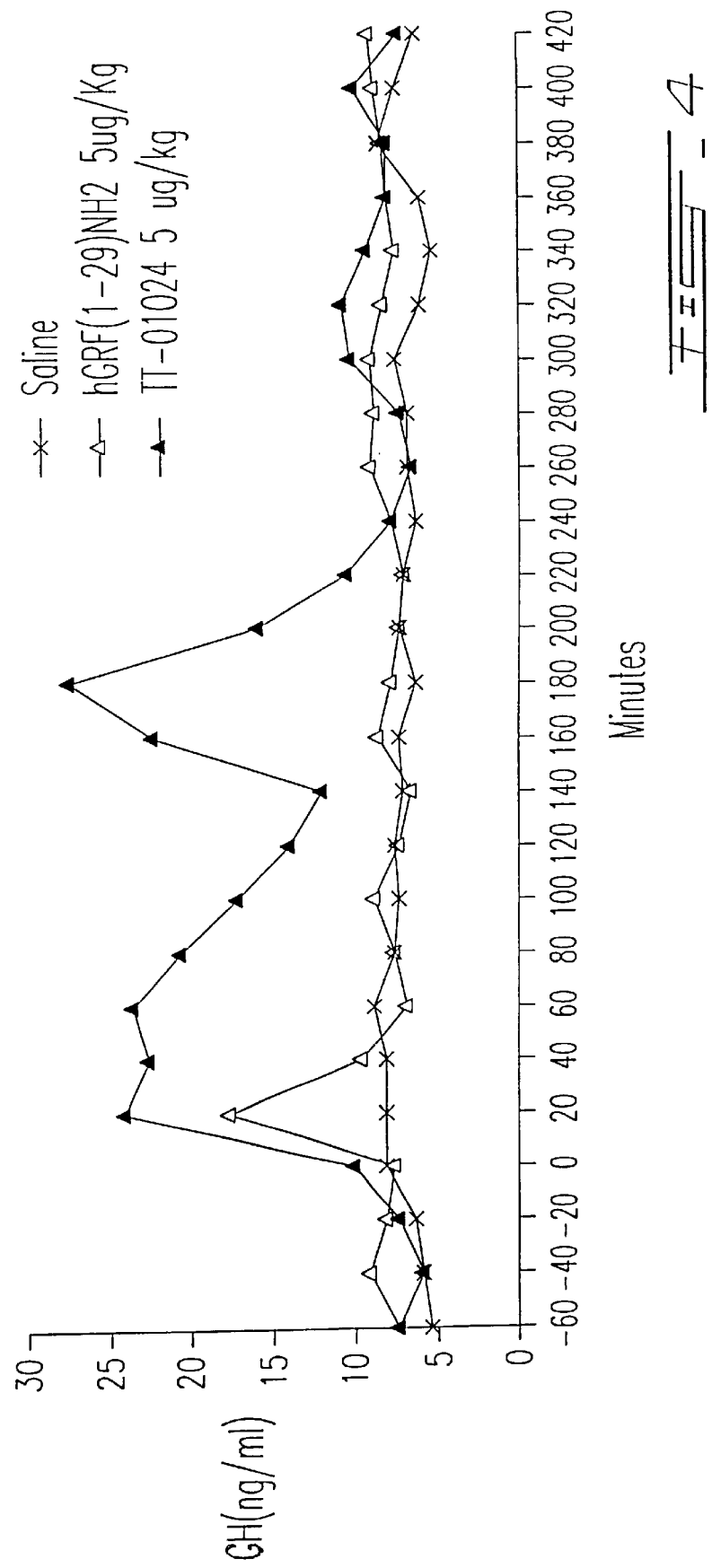
FIG. 4 is a curve of the effect of one subcutaneous injection of 5 μg/kg hGRF(1-29)NH$_2$ and (5 μg/kg) (Hexenoyl trans-3)° hGRF (1-29)NH$_2$ analog on pig serum GH.
Figure 5:
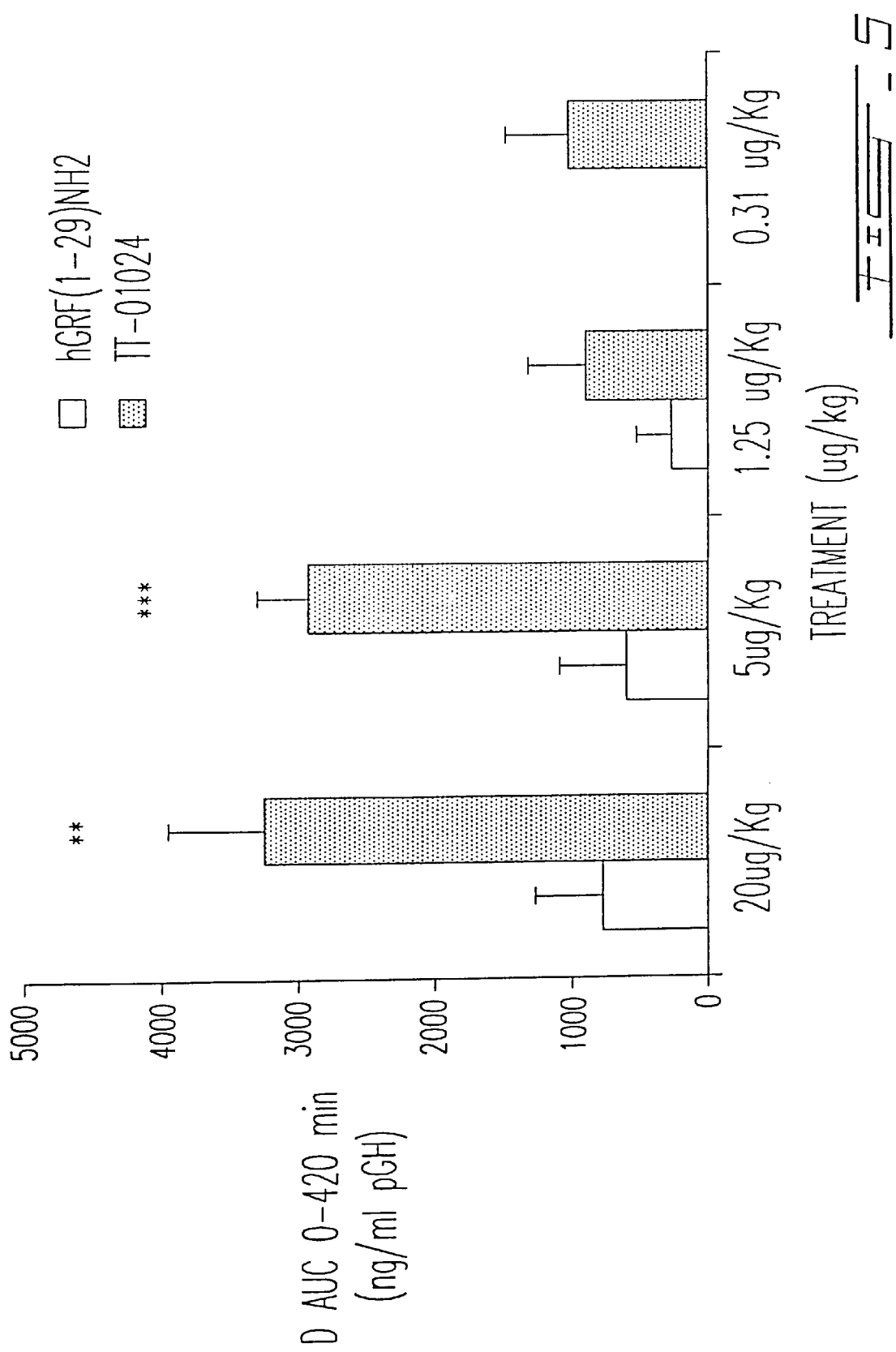
FIG. 5 is a graph showing the effect of various doses of hGRF(1-29)NH$_2$ vs [Hexenoyl trans-3]° hGRF(1-29)NH$_2$ (TT-01024) on the GH area under the curve over 420 minutes following S.C. administration (P<0.01 and *P<0.001 when compared to the basal period —60 to 0 mm–)

Results are shown in FIGS. 4 and 5. As shown in FIG. 4, the subcutaneous injection of 5 μg/kg hGRF(1-29)NH₂ induced a GH response in the first 60 minutes following administration, whereas the same injection of hexenoyl trans3-hGRF(1-29)NH₂ induced a GH response that was sustained for 240 minutes. The FIG. 5 illustrates the effect of various doses of the GRFs tested on the OH area under the curve over the study period, i.e. from 0 to 420 minutes following injection. Over this period, hGRF(1-29)N112 did not induce any significant GH response at any of the tested doses, whereas hexenoyl trans3-hGRF(1-29)NH₂ elicited significant increases of the GH AUC at 5 and 20 μg/kg. Altogether, these results suggest that hexenoyl trans3-hGRF (1-29)NH₂ is a highly potent OH secretagogue, even when subcutaneously administered.

EXAMPLE V

In accordance with a preferred embodiment of the present invention there is provided a hydrophobic GRF analog of formula A:

$$X—GRF\text{-peptide} \quad (A)$$

wherein;

the GRF peptide is a peptide of formula B;

A1–A2-Asp-Ala-Ile-Phe-Thr-A8-Ser-Tyr-Arg-Lys-A13-Leu-A15-Gln-Leu-A18-Ala-Arg-Lys-Leu-Leu-A24-A25-Ile-A27-A28-Arg-A30-R$_0$   (B)

wherein,
A1 is Tyr or His;
A2 is Val or Ala;
A8 is Asn or Ser;
A13 is Val or Ile;
A15 is Ala or Gly;
A18 is Ser or Tyr;
A24 is Gln or His;
A25 is Asp or Glu;
A27 is Met, Ile or Nle;
A28 is Ser or Asn;
A30 is a bond or any amino acid sequence of 1 to 15 residues;
R$_0$ is NH$_2$ or NH-(CH$_2$)n-CONH$_2$, with n=1 to 12 and;
X is cis or trans CH$_3$—CH$_2$—CH=CH—CH$_2$—CO—, or one element selected from a cis or a trans enantiomer or a racemic mixture of

1

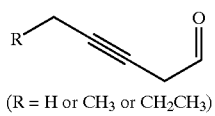

(R = H or CH$_3$ or CH$_2$CH$_3$)

2

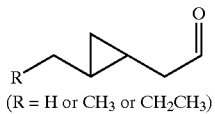

(R = H or CH$_3$ or CH$_2$CH$_3$)

3

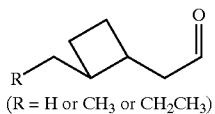

(R = H or CH$_3$ or CH$_2$CH$_3$)

4

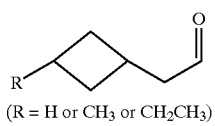

(R = H or CH$_3$ or CH$_2$CH$_3$)

5

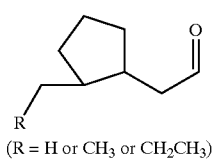

(R = H or CH$_3$ or CH$_2$CH$_3$)

6

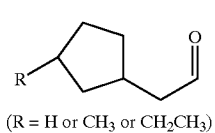

(R = H or CH$_3$ or CH$_2$CH$_3$)

7

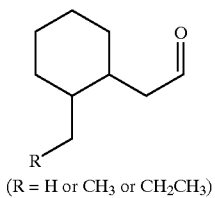

(R = H or CH$_3$ or CH$_2$CH$_3$)

8

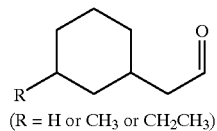

(R = H or CH$_3$ or CH$_2$CH$_3$)

9

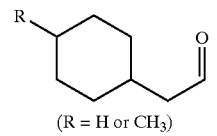

(R = H or CH$_3$)

10

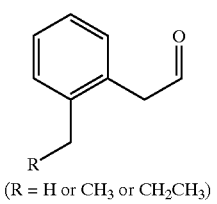

(R = H or CH$_3$ or CH$_2$CH$_3$)

11

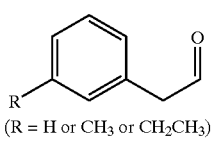

(R = H or CH$_3$ or CH$_2$CH$_3$)

12

(R = H or CH$_3$)

13

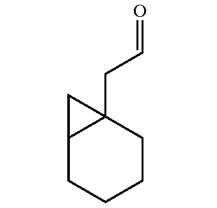

wherein R is a hydrogen or a lower alkyl.

Figure 6B:
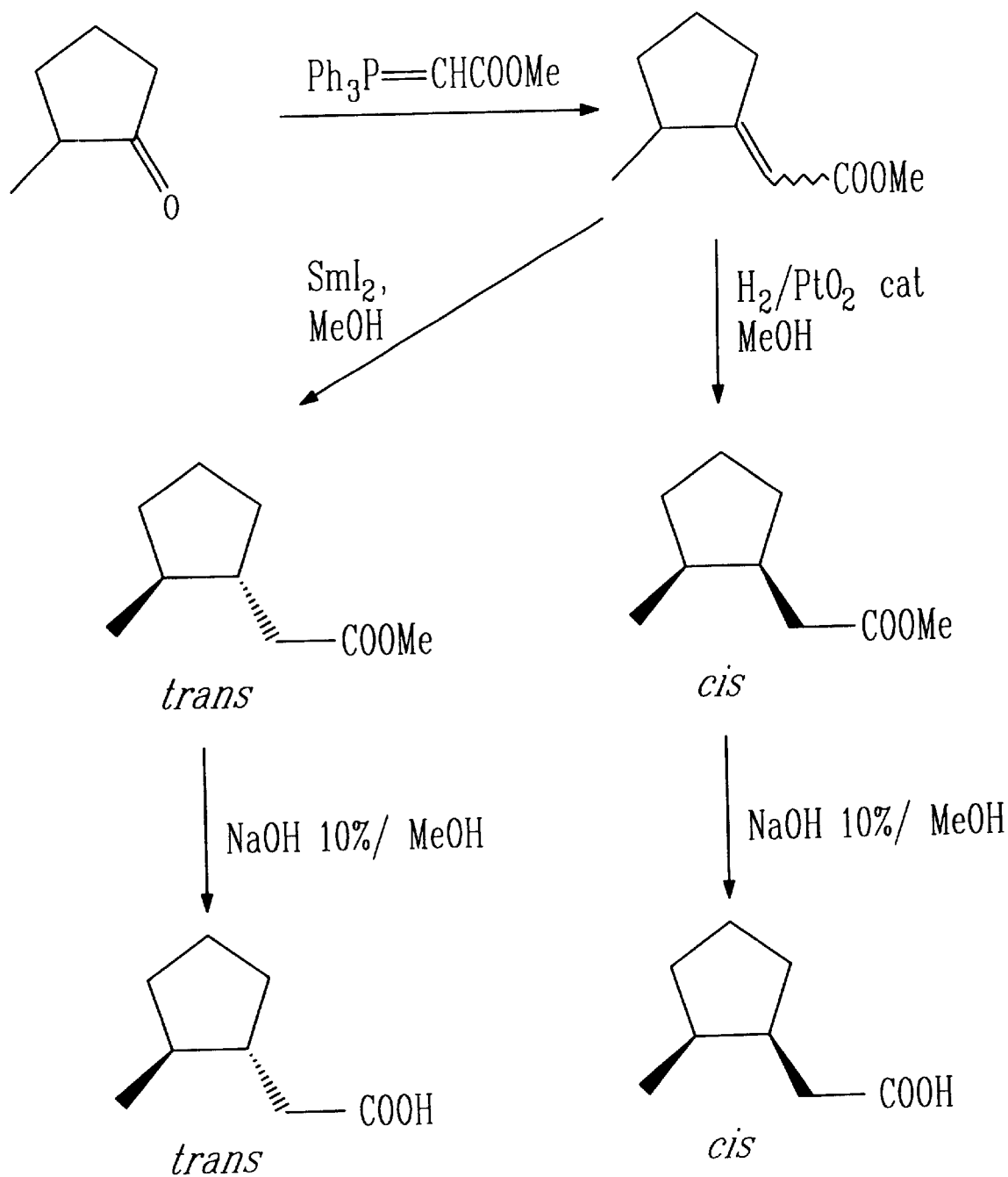
Figure 6C:
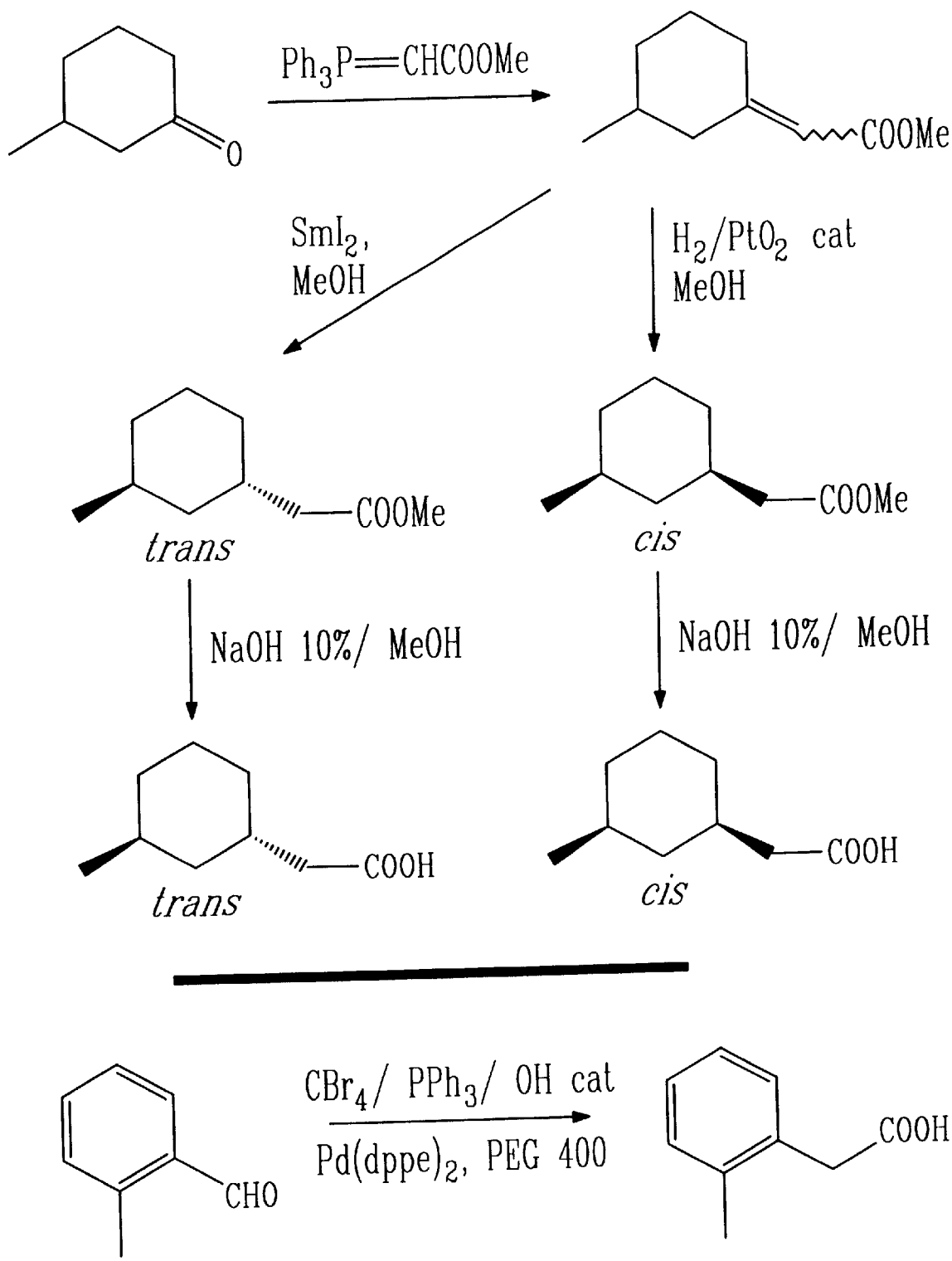

FIG. 6A to 6C illustrate examples of specific synthesis of the X-portion of GRF analogs with preferred radicals R in accordance with the present invention.

The acyl radicals X identified above with the numerals 10 (R=CH$_3$), and 11 (R=CH$_3$) are derived from the precursor carboxylic acids (X-OH) sold by Aldrich under catalog numbers T3,808-3 and T3,809-1.

EXAMPLE VI

Synthesis of (+,−)-cis-2-Ethylcyclopropylacetic Acid (15)

Synthesis of (+,−)-cis-2-ethylcyclopropylacetic acid (15) was accomplished as illustrated in scheme 1. First the cis-3-hexen-1-ol was reacted with diethyl zinc in presence of chloroiodomethane (Scott E. Denmark and James P. Edwards *J. Org. Chem.* 1991, 56, 6974–6981) in dichloromethane at 0° C. to give the desired cyclopropyl alcohol 14 in 92% yield. Oxidation of the alcohol 14 with pyridinium dichromate (Corey, E. J. and Schmidt, G. *Tetrahedron Lett.* 1979, 399–402) in dry DMF gave the (+,−)-cis-2-ethylcyclopropylacetic acid (15) in 66% yield.

Scheme 1

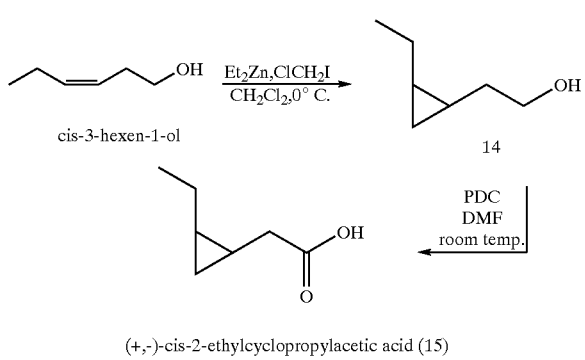

(+,−)-cis-2-ethylcyclopropylacetic acid (15)

Preparation of (+,−)-cis-2-Ethylcyclopropylacetic Acid (15)

1. Preparation of Cyclopropyl Alcohol 14

In a 250 ml, one necked flask, a solution of Et$_2$Zn (4.0 ml; 40 mmol; 2 eq.) in dry dichloromethane (70 ml) was cooled to 0° C., and a solution of ClCH$_2$I (5.8 ml; 80 mmol; 4 eq.) was added via seringe. The solution was stirred for 5 min at 0° C., during which time a precipitate was formed, and a solution of cis-3-hexen-1-ol (2.0 g, 20 mmol) in CH$_2$Cl$_2$ (32 ml) was added via cannula. The reaction mixture was stirred for 90 min at 0° C. and quenched with a saturated aqueous solution of NH$_4$Cl (100 ml). The solution was then allowed to warm to room temperature, stirred vigorously for 10 min, and extracted with dichloromethane (3×60 ml). The extracts were washed with H$_2$O (1×20 ml) and brine (1×20 ml), combined, dried (MgSO$_4$), and concentrated under reduced pressure. The residue was purified by silica gel chromatography (hexane/AcOEt, 8/2) to afford 2.10 g (92.3%) of the desired product 14 as a clear, colorless liquid. Rf=0.22 (hexane/AcOEt, 8/2) Characterization: Nmr ($^1$H, $^{13}$C), ir, ms 2. Preparation of (+,−)-cis-2-Ethylcyclopropylacetic Acid (15)

Alcohol 14 (2.30 g; 19.8 mmol) was dissolved in dry DMF (96 ml) and pyridinium dichromate (PDC) (3.5 eq., 26 g) was added in one portion. The reaction mixture was stirred overnight at room temperature and then poured into 300 ml of water and extracted with (4×80 ml) of ether. The organic layers were combined, washed with brine and concentrated under reduced pressure. The residue was then dissolved in chloroform (30 ml) and the solution was extracted two times with 25 ml of a 10% aqueous solution of NaOH. Combined aqueous phases were then extracted with chloroform (2×25 ml) and acidified with 10% aqueous HCl followed by an extraction with ether (4×50 ml). The combined organic phases were dried over MgSO$_4$, filtered and concentrated under reduced pressure to give the desired product (+,−)-cis-2-ethylcyclopropylacetic acid (15) as a colorless oil (1.7 g, 66%) Characterization: Nmr ($^1$H, $^{13}$C), ir, ms

EXAMPLE VII

Synthesis of (1R,2S)-2-Ethylcyclopropylacetic Acid (22) and (1R,2R)-2-Ethylcyclopropylacetic Acid (24)

The synthesis of the optically pure cis and trans acids (1R,2R)-2-ethylcyclopropylacetic acid (24) and (1R,2S)-2-ethyl-cyclopropylacetic acid (22) was accomplished according to the protocol of Charette.(Charette, A. B.; Juteau, H.; Lebel, H.; and Molinaro C. J. Am. Chem. Soc. 1998, 120, 11943–11952) To achieve this, the chiral dioxaborolane ligand 20 was required.

1. Synthesis of the Dioxaborolane Ligand 20

The synthesis (scheme 2) began with the preparation of butyl boronic acid 18 via the treatment of butyl magnesium bromide with trimethyl borate followed by acidic hydrolysis. To avoid the dehydration of butyl boronic acid and its transformation into boroxine, it was converted to its diethanolamine complex 19. (R,R)-(+)-N,N,N,'N,'-tetramethyl tartaric acid diamide 16 was easily prepared using Seebach's procedure (Seebach, D.; Kalinowski, H.-O.; Langer, W.; Wilka, E.-M. *Organic Syntheses*; Wiley: New York, 1990; Coll. Vol. VII, pp 41–50) by condensing (R,R)-(+)-dimethyl tartaric acid with dimethyl amine.

The diethanolamine complex 19, when treated with a slight excess of (R,R)-(+)-N,N,N,'N,'-tetramethyl tartaric acid diamide (16) in a biphasic medium, reacted to give the desired chiral dioxaborolane ligand 20 in 93% yield.

Scheme 2

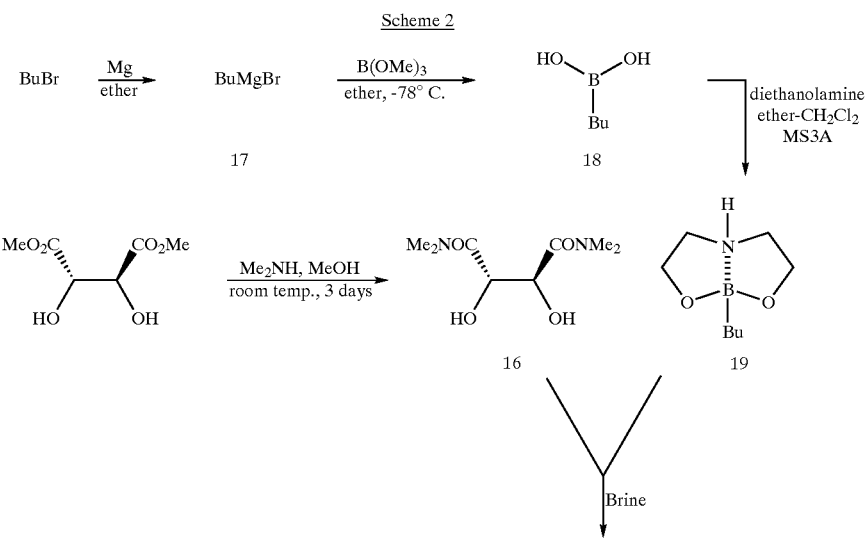

-continued

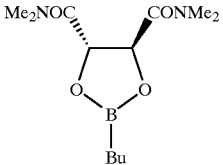

20

2. Synthesis of (1R,2S)-2-Ethylcyclopropylacetic Acid (22)

Once the dioxaborolane ligand 20 was in hand, we proceeded with the synthesis of (1R,2S)-2-ethylcyclopropylacetic acid (22) as shown in scheme 3. Thus, the homoallylic alcohol trans-3-hexen-1-ol was added to a mixture of the dioxaborolane 20 ligand and the zinc reagent ($Zn(CH_2I)_2$·DME) (obtained from the mixture of $Et_2Zn$, $CH_2I_2$ and DME) in dichloromethane at −10° C. The homogenous mixture was then warmed to room temperature and stirred overnight. Non-oxidative work-up afforded the desired product 21 in 79% yield, after a Kugelrohr distillation. Finally, pyridinium dichromate (PDC) oxidation of alcohol 21 gave the (1R,2S)-2-ethylcyclopropylacetic acid (22) in 39.7% yield (scheme 3).

Scheme 3

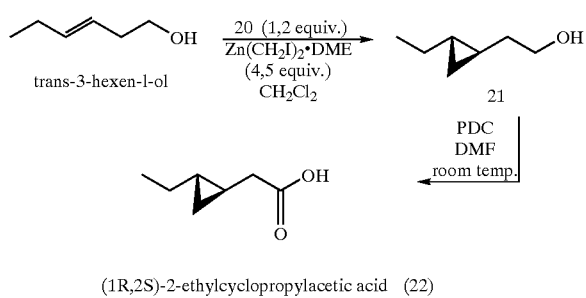

(1R,2S)-2-ethylcyclopropylacetic acid (22)

3. Synthesis of (1R,2R)-2-Ethylcyclopropylacetic Acid (2)

The synthesis of optically active (1R,2R)-2-ethylcyclopropylacetic acid (24) (scheme 4), was accomplished by using the same method used to produce (1R,2S)-2-ethylcyclopropylacetic acid (22).

Scheme 4

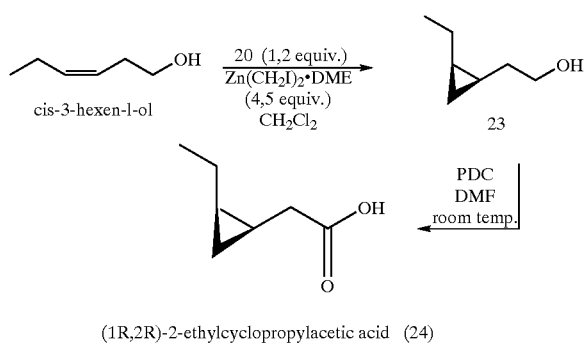

(1R,2R)-2-ethylcyclopropylacetic acid (24)

Preparation of (1R,2S)-2-Ethylcyclopropylacetic Acid (I2) and (1R,2R)-2-Ethylcyclopropylacetic Acid (24)

1. Preparation of Dioxaborolane Ligand 20
1.1 Preparation of Butylmagnesium Bromide 17

To a 1L, three-necked, round-bottomed flask equipped with a magnetic stirrer, a 125-mL, pressure-equalizing addition funnel, a reflux condenser and a glass stopper, is added 34.0 g (1.40 mol) of magnesium turnings. The agitation is started and the system is flame-dried for 2 min. The flask is then cooled to room temperature under a flow of nitrogen and 60 ml of ether is introduced to cover the magnesium. A solution of 48 ml (0.44 mol) of bromobutane in 140 ml of ether is placed in the pressure-equalizing addition funnel. The mixture is heated gently to initiate the reaction. When the reaction has started, the solution of bromide in ether is added dropwise at a rate sufficient to maintain a gentle reflux. After the completion of the addition, the funnel is rinsed with 10 ml of ether. The gray solution is stirred for 20 min and then transferred to a dry flask under nitrogen via cannula. The Grignard reagent is titrated with a solution of isopropanol in benzene using 1,1 0-phenanthroline as indicator as follows: a dry 10-ml, one necked, round-bottomed flask is charged with 1 ml of Grignard reagent, some drops of dry THF and a crystal of 1,10-phenanthroline. The slightly pink solution is titrated with a solution 0.5 M of isopropanol in dry benzene. Between 3.8 and 4.2 ml are obtained to give a clear colorless solution (3 titrations). A solution of Grignard reagent of 1.90–2.00 M is obtained.

1.2 Preparation of Butyl Boronic Acid 18

To a 1-L, three-necked, round bottomed flask equipped with a magnetic stirrer and thermometer, was added 480 ml of ether, followed by 20 ml (176 mmol) of trimethylborate. The clear solution was cooled to −75° C. (internal temperature) and vigorously stirred, then 90 ml (176 mmol) of 1.95 M solution of butylmagnesium bromide in ether was added dropwise via cannula at such a rate that the internal temperature did not exceed −65° C. After the addition was completed, the resulting white slurry was stirred for an additional 2 hours at −75° C. under nitrogen. The cooling bath was then removed and the reaction mixture was allowed to warm to room temperature (between 1h and 2h are needed). Hydrolysis was carried out by the dropwise addition of 200 ml of a 10% aqueous solution of hydrochloric acid. The white precipitate was dissolved and the resulting clear biphasic mixture was stirred for 15 min, after which time, the two layers were separated. The aqueous layer was extracted with ether (2×100 ml), and the combined extracts dried over magnesium sulfate. After concentration of the ethereal solution under reduced pressure, the residual white solid was purified by recrystallization as follows: after dissolution in hot water (50 ml), the resulting biphasic solution was cooled to 0° C. to induce recrystallization of the boronic acid. The solid was collected on a medium fritted disk funnel and washed with 100 ml of hexanes and placed under vacuum for 60 min. A quantity of 13.6 g of the boronic acid 18 was produced as a white solid.

Yield: 74.88%; m.p.=94–96° C. (lit. m.p.=95–97° C.) (Charette, A. B.; Juteau, H.; Lebel, H.; and Molinaro C. J. Am. Chem. Soc. 1998, 120, 11943–11952); Characterization: Nmr ($^1$H).

1.3 Preparation of [(2-)-N,O,O'[2,2'-Iminobis[ethanolato]]]-2-butyl boron 19

A 1-L, one-necked, round-bottomed flask equipped with a magnetic stirrer and thermometer, and under nitrogen, was charged with 13,6 g (133 mmol) of the butylboronic acid 18 and 14,0 g (134 mmol) of diethanolamine. Then, 133 ml of dichloromethane and 265 ml of ether were added, followed by about 27 g of molecular sieve 3 Å (powder, dried in an oven overnight at 250° C.). The resulting heterogeneous solution was stirred for 1 day under nitrogen. The solid was then triturated with dichloromethane (2×100 ml). The filtrate was concentrated under reduced pressure to produce the crude desired complex. The diethanolamine complex was purified by recrystallization as follows: the white solid was dissolved in hot dichloromethane (40 ml), then ether (100 ml) was added to induce crystallization of the complex. The mixture was then cooled to 0° C. and the solid was collected on a medium fritted disk funnel and washed with ether (2×60 ml). The product was dried under vacuum to afford 18.31 g of the title compound 19 as a white crystalline solid.

Yield: 80%; m.p.=143–145° C. (lit. m.p.=145–148° C.) (Charette, A. B.; Juteau, H.; Lebel, H.; and Molinaro C. *J. Am. Chem. Soc.* 1998, 120, 11943–11952). Characterization: Nmr ($^1$H).

1.4 Preparation of (R,R)-(+)-N,N,N,'N,'-Tetramethyl Tartaric Acid Diamide 16

Into a mixture of 68 g (381 mmol) of dimethyl tartrate and 77 ml of methanol spectrograde in a 250 ml Erlenmeyer flask was poured at least 100 ml of liquid, anhydrous, cold (−78° C.) dimethylamine (obtained from the condensation of dimethylamine gas at −78° C.). The mixture was swirled briefly and allowed to stand in a hood for 3 days with a drying tube in place. After crystallization, the massive crystals were collected by suction filtration. The filtrate was concentrated, seeded, and cooled to yield a second crop. Combined crystals were washed with cold methanol (−30° C.) and dried under vacuum. The diamide 16 thus obtained was sufficiently pure to be used in the following step.

Yield: 90%; m.p.=188–189° C. (lit.189–190° C.) (Seebach, D.; Kalinowski, H.-O.; Langer, W.; Wilka, E.-M. Organic Syntheses; Wiley: New York, 1990;

Coll. Vol. VII, pp 41–50); Characterization: Nmr ($^1$H).

1.5 Preparation of (4R-trans)-2-butyl-N,N,N',N'-Tetramtyl [1,3,2]dioxa-borolane [4,5]dicarboxamide 20

A 500 mL, one-necked, round-bottomed flask equipped with a magnetic stirrer, and under nitrogen, was charged with 7.00 g (40.9 mmol) of butylboronate diethanolamine 19 complex and 11 g (53.8 mmol) of (R,R)-(+)-N,N,N',N'-tetramethyltartaric acid diamide 16. The solids were dissolved upon addition of 205 ml of dichloromethane. Then, 64 ml of brine was added and the resulting biphasic solution was stirred for 2 h 45 min under nitrogen. The two layers were separated and the aqueous layer extracted with dichloromethane (50 ml). The combined organic layers were washed with brine (50 ml), dried over MgSO$_4$ and filtered. The filtrate was concentrated under reduced pressure and dried vacuum to afford 10,2 g of the title compound 20 as a pale yellow oil.

Yield: 92% (lit. 93%) (Charette, A. B.; Juteau, H.; Lebel, H.; and Molinaro C. *J. Am. Chem. Soc.* 1998, 120, 11943–11952).

Characterization: Nmr ($^1$H, $^{13}$C), ir, ms).

2. Preparation of (1R,2S)-2-Ethylcyclopropylacetic Acid (22)

2.1 (1R,2S)-2-Ethylcyclopropylethanol 21

A 250-mL, three-necked, round bottomed flask equipped with a magnetic stirrer and a thermometer, and under nitrogen, was charged with 45 ml of dry CH$_2$Cl$_2$ and 4.6 ml (45 mmol, 4.5 eq.) of dry DMB. The solution was cooled to −10° C.(internal temperature) with an acetone/ice bath and 4.6 ml (45 mmol, 4.5 eq.) of Et$_2$Zn was added. To this stirred solution was added 7.2 ml (90 mmol, 9 eq.) of CH$_2$I$_2$ over a 1 hour period while maintaining the internal temperature between −8 and −12° C. After completion of the addition, the resulting solution was stirred for 10 min at −10° C. A solution of 3.36 g (10.8 mmol, 1.2 eq.) of the dioxaborolane 20 ligand in 10 ml of CH$_2$Cl$_2$ was added via cannula under nitrogen over a 5–6 min period while maintaining the internal temperature below −5° C. A solution of 1.00 g (10 mmol) of cis-3-hexen-1-ol in 10 ml of CH$_2$Cl$_2$ was immediately added via cannula under nitrogen over a 5–6 min period while maintaining the internal temperature below −5° C. The cooling bath was removed and the reaction mixture allowed to warm to room temperature and stirred overnight at that temperature.

The reaction was quenched with saturated aqueous NH$_4$Cl (10 ml) and 10% aqueous HCl (40 ml). The two layers were separated and the aqueous layer was washed with CH$_2$Cl$_2$ (50 ml). The combined organic layers were transferred into an Erlenmeyer flask and a solution of 5 M aqueous KOH (200 ml) was added. The resulting biphasic solution was stirred vigorously overnight.

The two layers were then separated and the organic layer was successively washed with saturated aqueous NH$_4$Cl (3×50 ml) and brine (10 ml), dried over MgSO$_4$, filtered and concentrated under reduced pressure. The residue was purified by flash chromatography (AcOEt/hexanes 2/8) followed by Kugelrohr distillation (150–160° C.) to provide the desired cyclopropane derivative 21 (0.9 g).

Rf=0,33 (AcOEt/hexanes 2/8); Yield: 79%; $[\alpha]_D$=+15.60° (c=1.66, CHCl$_3$); Characterization: Nmr ($^1$H, $^{13}$C), ir, ms.

2.2 Preparation of (1R,2S)-2-Ethylcyclopropylacetic Acid (22)

A 250-mL, one-necked, round bottomed flask equipped with a magnetic stirrer, and under nitrogen, was charged with 1.65 g (14.3 mmol) of alcohol 21 and 40 ml of dry DMF. Pyridinium dichromate 18.8 g (3.5 eq.; 50.1 mmol) was added in one portion. The reaction mixture was stirred overnight at 25° C. and then poured into 200 ml of water and extracted with ether (4×80 ml). The organic layers were concentrated under reduced pressure, and the residue was then dissolved in chloroform (50 ml) and extracted with a 10% aqueous NaOH (2×25 ml). The combined aqueous layers were washed twice with 25 ml of chloroform, followed by acidification with a 10% aqueous HCl. Extraction with ether (4×50 ml), drying over MgSO$_4$, filtration and concentration under reduced pressure afforded the desired compound (1R,2S)-2-ethylcyclopropylacetic acid (22) as a colorless oil (737 mg).

Yield: 39.7%; $[\alpha]_D$=+7.7° (c=3.5, CHCl$_3$); Characterization: Nmr ($^1$H, 13C), ir, ms.

3. Preparation of (1R,2R)-2-Ethylcyclopropylacetic Acid (24)

3.1 (1R,2R)-2-ethylcyclopropylethanol 23

A 250-mL, three-necked, round bottomed flask equipped with a magnetic stirrer and a thermometer, and under nitrogen, was charged with 45 ml of dry CH$_2$Cl$_2$ and 4.67 ml (45 mmol, 4.5 eq.) of dry DME. The solution was cooled to −10° C.(internal temperature) with an acetone/ice bath and 4.6 ml (45 mmol, 4.5 eq.) of Et$_2$Zn were added. To this stirred solution was added 7.2 ml (90 mmol, 9 eq.) of CH$_2$I$_2$ over a 1 hour period while maintaining the internal temperature between −8 and −12° C. After completion of the addition, the resulting solution was stirred for 10 min at −10°

C. A solution of 3.36 g (10.8 mmol, 1.2 eq.) of the dioxaborolane 20 ligand in 10 ml of $CH_2Cl_2$ was added via cannula under nitrogen over a 5–6 min period while maintaining the internal temperature below −5° C. A solution of 1.00 g (10 mmol) of trans-3-hexen-1-ol in 10 ml of $CH_2Cl_2$ was immediately added via cannula under nitrogen over a 5–6 min period while maintaining the internal temperature below −5° C. The cooling bath was removed and the reaction mixture allowed to warm to room temperature and stirred overnight at that temperature.

The reaction was quenched with saturated aqueous $NH_4Cl$ (10 ml) and 10% aqueous HCl (40 ml). The two layers were separated and the aqueous layer was washed with $CH_2Cl_2$ (50 ml). The combined organic layers were transferred into an Erlenmeyer flask and a solution of 5 M aqueous KOH (200 ml) was added. The resulting biphasic solution was stirred vigorously overnight.

The two layers were then separated and the organic layer was successively washed with saturated aqueous $NH_4Cl$ (3×50 ml) and brine (10 ml), dried over $MgSO_4$, filtered and concentrated under reduced pressure. The residue was purified by flash chromatography (AcOEt/hexanes 2/8) followed by Kugelrohr distillation (150–162° C.) to provide the desired cyclopropane derivative 23 (1.06 g).

Rf=0.33 (AcOEt/hexanes 2/8); Yield: 93%; $[\alpha]_D$=+6.220 (c=2.25, $CHCl_3$) (lit.$[\alpha]_D$=+9.60 (c=0.3, $CHCl_3$); (Charette, A. B.; Juteau, H.; Lebel, H.; and Molinaro C. J. Am. Chem. Soc. 1998,120, 11943–11952). Characterization: Nmr ($^1H$, $^{13}C$), ir, ms.

3.2 Preparation of (1R,2R)-2-Ethylcyclopropylacetic Acid (24)

A 250-mL, one-necked, round bottomed flask equipped with a magnetic stirrer, and under nitrogen, was charged with 1.7 g (14.9 mmol) of alcohol 23 and 40 ml of dry DMF. Pyridinium dichromate 19.6 g (3.5 eq.; 52.1 mmol) was added in one portion. The reaction mixture was stirred overnight at 25° C. and then poured into 200 ml of water and extracted with ether (4×80 ml). The organic layers were concentrated under reduced pressure, and the residue was then dissolved in chloroform (50 ml) and extracted with a 10% aqueous NaOH (2×25 ml). The combined aqueous layers were washed twice with 25 ml of chloroform, followed by acidification with 10% aqueous HCl. Extraction with ether (4×50 ml), drying over $MgSO_4$, filtration and concentration under reduced pressure afforded the desired compound (1R,2R)-2-ethylcyclopropylacetic acid (24) as a colorless oil (1.05 g).

Yield: 55.5%; $[\alpha]_D$=+4.360 (c=1.83, $CHCl_3$); Characterization: Nmr ($^1H$, $^{13}C$), ir, ms.

EXAMPLE VII

Synthesis of a (1:1) Mixture of (1S,3R) and (1R, 3R)-3-Methylcyclopentylacetic Acid (27)

The (1:1) mixture of (1S,3R) and (1R,3R)-3-methylcyclopentylacetic acid (27) was synthesized according to the outline in scheme 5. A Wittig-Horner (Duraisamy, M. and Walborsky H. M. J. Am. Chem. Soc 1983, 105, 3252–3264) reaction involving condensation of 25 (R)(+)-3-methyl cyclopentanone and triethyl phosphonoacetate gave a (1:1) mixture of ethyl (E, and Z,3R)-(3-methyl cyclopentylidene) carboxylate 25. Hydrogenation of the α,β-unsaturated ester 25 proceeded without stereocontrol, and a (1:1) mixture of the ester 26 was obtained in quantitative yield. Hydrolysis of the ester 26 with alcoholic KOH afforded a (1:1) mixture of the desired (1S,3R) and (1R, 3R)-3-methylcyclopentylacetic acid (27) in 92% yield.

Scheme 5

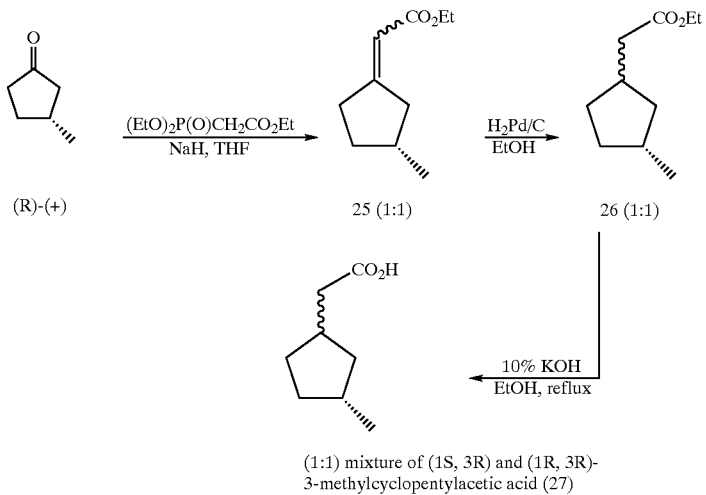

(1:1) mixture of (1S, 3R) and (1R, 3R)-3-methylcyclopentylacetic acid (27)

Preparation of a (1:1) Mixture of (1S,3R) and (1R,3R)-3-Methylcyclopentylacetic Acid (27)

1. Preparation of α,β-unsaturated ester 25

To a dry 100 ml, one necked, round-;bottomed flask equipped with a magnetic stirrer, was added 611 mg (15.8 mmol) of 60% sodium hydride as a dispersion in mineral oil. The oil was removed by washing twice with pentane. Dry THF (21 ml) was added and the suspension, maintained under nitrogen atmosphere. After cooling the flask to 0° C. in an ice bath, 3.43 g (15.2 mmol) of triethyl phosphonoacetate was slowly added. Stirring was continued for 35 min, and R-(+)-3-methylcyclopentanone (1.51 g; 15.2 mmol) was then added, and the temperature was kept at room temperature for an additional hour, during which time a gelatinous precipitate appeared. Ether (100 ml) and water (50 ml) were added to quench the reaction. The mixture was transferred to a separatory funnel and washed twice with water and then with brine. The organic solution was dried over $MgSO_4$, filtered and concentrated under reduced pressure. The residue was purified by flash chromatography (hexane/AcOEt, 9/1) to afford 2.4 g (96%) of the desired product 25 as a clear, colorless oil.

Rf=0.53 (hexane/AcOEt, 9/1); Characterization: Nmr ($^1$H, $^{13}$C), ir, ms.

2. Preparation of Ester 26

To a stirred solution of α,β-unsaturated ester 25 (1.3 g; 7.7 mmol) in anhydrous ethanol (68 ml) was added 163 mg of 10% palladium on carbon. The mixture was stirred overnight under an atmosphere of hydrogen. The catalyst was then removed by filtration on a pad of celite. The filtrate was concentrated and the residue, ester 26, a colorless oil, was used without purification for the next step.

Yield: (1.2 g) 92%. Characterization: Nmr ($^1$H, 13C), ir, ms.

3. Preparation of a (1:1) Mixture of (1S,3R)- and (1R,3R)-3-methyl Cyclopentylacetic Acid (27)

To the ester 26 (1.20 g; 7.05 mmol) in ethanol (50 ml) was added 15 ml of a 10% aqueous solution of potassium hydroxide. The reaction mixture was stirred under reflux for 5 hours. The ethanol was then evaporated in vaccuo and the residue extracted with ether (20 ml). The aqueous phase was acidified with 10% aqueous HCl and extracted with ether (3×50 ml). The combined organic phases were then dried over MgSO$_4$, filtered and concentrated under reduced pressure to give a (1:1) mixture of (1S,3R)- and (1R,3R)-3-methyl cyclopentylacetic acid (27) as a colorless oil (920 mg) in 92% yield. Characterization: Nmr ($^1$H, $^{13}$C), ir, ms

EXAMPLE VIII

Synthesis of Bicyclo[4.1.0]heptylacetic Acid (31)

The compound 31 was prepared in four steps as outlined in scheme 6. Application of the Wittig-Homer procedure (Duraisamy, M. and Walborsky H. M. *J. Am. Chem. Soc* 1983, 105, 3252–3264) to cyclohexanone with triethyl phosphonoacetate (NaH, THF) provided the α,β-unsaturated ester 28 in 88% yield. The desired β,γ-unsaturated ester 29 could be prepared from the α,β-unsaturated ester 28 by kinetic trapping of the extended enolate (LDA, THF) with saturated aqueous NH$_4$Cl at −78° C. Cyclopropanation (Scott E. Denmark and James P. Edwards *J. Org. Chem.* 1991, 56, 6974–6981) with diethylzinc/chloroiodomethane in dichloromethane at 0° C. produced the cyclopropyl 30 in 91.5% yield. Saponification of ester 30 in KOH/EtOH followed by subsequent acidification afforded 31 in 92% yield (Kantorowski, E. J.; Eisenberg, S. W. E.; Fink, W. H.; and Kurth, M. J. *J. Org. Chem.*, 1999, 64, 570–580).

Scheme 6

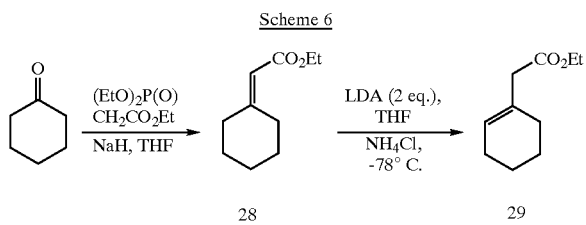

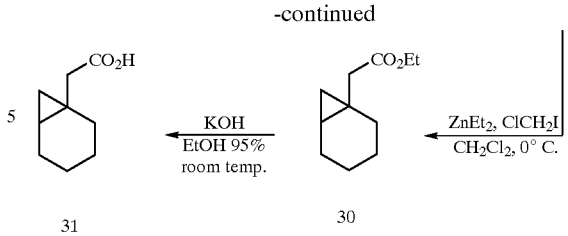

Preparation of Bicyclo[4.1.0]heptylacetic Acid (31)

1. Preparation of α,β-unsaturated Ester 28

To a dry 200 ml, one necked, round-bottomed flask equipped with a magnetic stirrer, was added 1.22 g (30.5 mmol) of 60% sodium hydride as a dispersion in mineral oil. The oil was removed by washing twice with pentane. Dry THF (50 ml) was added and the suspension, maintained under nitrogen atmosphere. After cooling the flask to 0° C. in an ice bath, 6.85 g (30.5 mmol) of triethyl phosphonoacetate was slowly added. Stirring was continued for 30 min, and cyclohexanone (3.00 g; 30.5 mmol) was then added, and the reaction mixture was kept at room temperature for an additional hour, during which time a gelatinous precipitate appeared. Ether (50 ml) and water (50 ml) were added to quench the reaction. The mixture was transferred to a separatory funnel and washed twice with water and then with brine. The organic solution was dried over MgSO$_4$, filtered and concentrated under reduced pressure. The residue was purified by flash chromatography (hexane/AcOEt, 9.5/0.5) to afford 4.52 g (88%) of the desired product 28 as clear, colorless oil.

Rf=0.56 (hexane/AcOEt, 9.5/0.5) Characterization : Nmr ($^1$H, $^{13}$C), ir, ms.

2. Preparation of β,γ-unsaturated Ester 29

To a solution of diisopropylamine (3.33 ml; 23.7 mmol) in dry THF (90 ml), kept at 0° C., was slowly added n-butyllithium ( 1.9 ml; 23.7 mmol). The solution was stirred for 20 min and then cooled to −78° C. The α,β-unsaturated ester 28 (2.00 g, 11.9 mmol) in THF (9 ml) was added dropwise over 10 min and the mixture was allowed to stir for 30 min at that temperature. Saturated aqueous NH$_4$Cl (20 ml) was added dropwise over a 10 min period, and the quenched reaction was allowed to warm to ambient temperature before being poured in water (10 ml) and extracted with ether (3×50 ml). The extracts were dried (MgSO$_4$), filtered and concentrated to afford a mixture of (4 : 1) β,γ-unsaturated: a,p-unsaturated ester (nmr) as a yellow oil. Flash chromatography (hexane/AcOEt, 9.65/0.35) afforded 1 g (50%) of the desired product 29 as clear, colorless oil.

Rf=0.44 (hexane/AcOEt, 9.5/0.5) Characterization: Nmr ($^1$H, $^{13}$C), ir, ms.

3. Preparation of Cyclopropyl Ester 30

In a 100 ml, one necked flask, a solution of Et$_2$Zn (1.27 ml; 11.0 mmol; 2 eq.) in dry dichloromethane (20 ml) was cooled to 0° C., and a solution of ClCH$_2$I (1.6 ml; 22 mmol; 4 eq.) was added via seringe. The solution was stirred for 5 min at 0° C., during which time a precipitate was formed, and a solution of β,γ-unsaturated ester 29 (924 mg, 5,49 mmol) in CH$_2$Cl$_2$ (8 ml) was added via cannula. The reaction mixture was stirred for 60 min at 0° C. and quenched with a saturated aqueous solution of NH$_4$Cl (60 ml). The solution was then allowed to warm to room temperature, stirred vigorously for 10 min, and extracted with ether (3×20 ml). The extracts were washed with H₂O (1×20 ml) and brine (1×20 ml), combined, dried (MgSO₄), and concentrated under reduced pressure. The residue was purified by flash chromatography (hexane/AcOEt, 9.5/0.5) to afford 915 mg (91.5%) of the desired product 30 as clear, colorless liquid.

Rf=0.44 (hexane/AcOEt, 9.5/0.5); Characterization: Nmr ($^1$H, $^{13}$C), ir, ms.

4. Preparation of Bicyclo[4.1.0]heptylacetic Acid (31)

Ester 30 (600 mg; 3.29 mmol) in basic ethanol (2.09 g KOH in 27 ml 95% ethanol) was stirred at room temperature overnight. The reaction was diluted with ether and extracted with NaOH ( 2 M, 2×50 ml), the combined extracts were acidified with aqueous 10% HCl and extracted with ether (3×40 ml). The combined organics were dried (MgSO₄), filtered and concentrated to give the desired 31 as a pale yellow liquid (467 mg; 92%). Characterization: Nmr ($^1$H, $^{13}$C), ir, ms

EXAMPLE IX

Synthesis of (1S, 3R)-3-Methylcyclohexylacetic Acid (36)

Finally, the synthesis of (1S, 3R)-3-methylcyclohexylacetic acid (36) was accomplished as depicted in scheme 7. First, (R)-(+)-3-methylcyclohexanone was reduced in 75% yield according to Brown's method (Brown, H. C.; Jadhav, P. K. In "Asymmetric Synthesis" Morisson, J. D., Ed.; Academic Press: New York, 1983; Vol. II, Chapter 1;

Brown, H. C.; Desai, M. C.; Jadhav, P. K. *J. Org. Chem.* 1982, 47, 5065–5069) to (3R,1R)-3-methylcyclohexanol 32.

The optically active 32 was mesylated and reacted with the sodium salt of dimethyl malonate in dry DMF at 80–90° C. to produce the desired diester 34 in 31% yield. Hydrolysis of the diester 34 with alcoholic KOH afforded the diacid 35 which upon decarboxylation under rather drastic conditions (concentrated H₂SO₄ in dioxane/water mixture under reflux for two days) gave the desired compound (1S, 3R)-3-methylcyclohexylacetic acid (36) in 74.8% yield.

Scheme 7

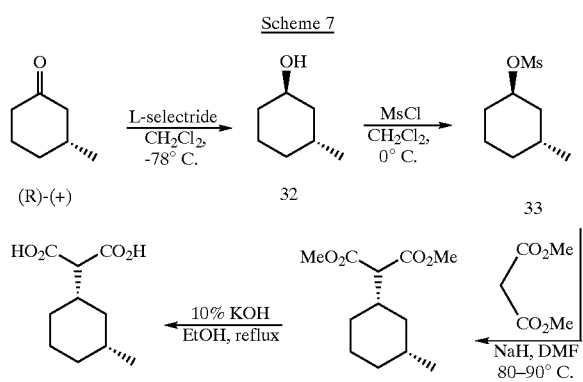

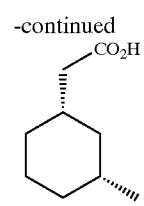

(1S,3R)-3-methylcyclohexylacetic acid (36)

Preparation of (1S, 3R)-3-Methylcyclohexylacetic Acid (36)

1. Preparation of Alcohol 32

A stirred solution of R-(+)-3-methylcyclohexanone (3.50 g; 31.1 mmol) in dry THF (40 ml) at −78° C. was treated with a 1.0 M solution of L-selectride in THF (63 ml; 63 mmol). After 2 hours of stirring at that temperature, a solution of 2 M aqueous sodium hydroxide (33 ml) was added followed by 23 ml of 30% H₂O₂. After warming to room temperature the reaction mixture was treated with 10% aqueous HCl and the product was isolated by extraction with ether (3×80 ml). The extracts were combined, dried over (MgSO₄), filtered and concentrated under vaccuo. The residue was purified by flash chromatography (hexane/AcOEt, 8/2) to afford 2.70 g (75%) of the desired product 32 as a clear, colorless oil.

Rf 0.52 (hexane/AcOEt, 8/2); $[\alpha]_D$=−2.90 (c=7.9; chloroform); Characterization: Nmr ($^1$H, $^{13}$C), ir, ms.

2. Preparation of Mesylate 33

To a stirred solution of (1R,3R)-(−)-3-methyl cyclohexanol (32) (1.27 g; 11.1 mmol) in dry dichloromethane (45 ml) were added Et₃N (2.3 eq.; 25.7 mmol; 3.58 ml) and methanesulfonyl chloride (1.2 eq.; 13.4 mmol; 1.00 ml) in a dropwise fashion at 0° C. The reaction mixture was stirred for 1 hour at 0° C., and then diluted with dichloromethane (80 ml) and 50 ml of 10% aqueous HCl. The aqueous phase was extracted with CH₂Cl₂ (50 ml). The combined organic layers were successively washed with saturated NaHCO₃ (1×20 ml) and brine (1×20 ml) and then dried over MgSO₄, filtered and concentrated in vaccuo to afford (2.13 g) of crude mesylate 33 as a yellow oil which was used without purification for the next step.

Rf=0.52 (hexane/AcOEt, 8/2); Characterization: Nmr ($^1$H, $^{13}$C);

3. Preparation of Diester 34

To a dry 200 ml, one necked, round-bottomed flask equipped with a magnetic stirrer, was added (3.5 eq.; 39 mmol; 1.16 g) of 60% sodium hydride as a dispersion in mineral oil. The oil was removed by washing twice with pentane. Dry DMF (30 ml) was added and the suspension, maintained under nitrogen atmosphere. After cooling the flask to 0° C. in an ice bath, dimethyl malonate (3.5 eq.; 39 mmol; 5.16 g) was added. Stirring was continued for 10 min, and a solution of the mesylate 33 in DMF (58 ml) was added via cannula. The mixture was then stirred and heated at 80–90° C. for 3 days. Water (50 ml) was then added and the mixture was transferred to a separatory funnel and extracted with ether (3×100 ml). The organics were dried over MgSO₄, filtered and concentrated under reduced pressure. The residue was purified by flash chromatography (hexane/AcOEt, 8/2) to afford 800 mg (31%) of the desired product 34 as clear, colorless oil.

Rf=0.49 (hexane/AcOEt, 8/2); Characterization: Nmr $^1$H;

4. Preparation of Diacid 35

To a solution of the diester 34 (800 mg; 3.50 mmol) in 53 ml of ethanol, was added 8 ml of a 10% aqueous solution of potassium hydroxide. The mixture was heated to reflux for 5 hours, then left under stirring overnight. Ethanol was evaporated under reduced pressure and the residue was diluted with water (10 ml) and extracted with ether (20 ml). The aqueous phase was acidified with 10% aqueous HCl, then extracted with ether (3×30 ml). After drying over $MgSO_4$, filtration and concentration under vaccuo we obtained a white crystalline solid which was used without purification for the next step.

Yield: (600 mg) 85.6%; Characterization: Nmr $^1$H ($CD_3OD$).

5. Preparation of (1S, 3R)-3-Methylcyclohexylacetic Acid (X6)

To the diacid 35 (800 mg, 4.00 mmol) was added 15 ml of dioxane, 5 ml of water and 2 ml of sulfuric acid. The mixture was then heated to reflux for 3 days. After cooling to room temperature and extraction with ether (3×30 ml), the combined organic phases were dried over $MgSO_4$, filtered and concentrated to give (1S, 3R)-3-methylcyclohexylacetic acid (36) as a yellow oil.

Yield: (467 mg) 74.8%; Characterization: Nmr ($^1$H, $^{13}$C), ir, ms.

EXAMPLE X

Formation of Hydrophobic GRF Analogs

The coupling of X moiety to GRF-peptide to result in the formation of the hydrophobic GRF analog of the present invention was chemically synthesized by anchoring one or several hydrophobic tails at the N- terminal portion of GRF or one of its analogs as described above.

More precisely, for a better carrying out of the chemical anchoring reaction, hydrophobic functionalized under the acid form are preferably used. In these conditions, the anchoring reaction is preferably effected in a solid phase (Merrifield R. B., 1963, J. Am. Chem. Soc., 85:2149; 1964, J. Am. Chem. Soc., 86:304) using extremely active reagents such as for example Benzotriazol-1-yloxytris (dimethylamino) phosphonium hexafluorophosphate known in the prior art (B. Castro et al., 1975, *Tetrahedron letters*, Vol. 14:1219).

In the case where the hydrophobic tail to be anchored consists in a fatty acid, the activation in view of the anchoring may be carried out in situ. Depending on the synthesis strategies used, the peptide anchoring site is liberated just prior to the anchoring in traditional deprotection conditions (Gross et Meienhofer, 1981, *The peptides*, vol. 3, Academic press: pages 1–341). The hydrophobic tail (Ht) is then condensed with the anchoring agent in organic solvents such as an ether (tetrahydrofuran), an aliphatic halogenated solvent (dichloromethane), a nitrile (acetonitrile) or an amide (N,N-dimethylformamide).

With respect to the anchoring dynamic, the preferred working temperatures are between 20 and 60° C. The anchoring reaction time when hydrophobic tail used are more and more hydrophobic, varies inversely with temperature, but varies between 0.1 and 24 hours.

General GRF analogs synthesis steps were carried out by solid-phase methodology on a 9050™ plus peptide synthesizer (Millipore Corporation, Milford, Mass.) using Fmoc strategy and synthesis cycles supplied by Millipore. Fmoc amino acids were supplied by Bachem California and other commercials sources. Sequential Fmoc chemistry using BOP/HOBt as coupling methodology were applied to the starting Fmoc-Pal-PEG resin (Millipore, catalog number: GEN 913383) for the production of C-terminal carboxamides. Fmoc deprotections were accomplished with piperidine 20% solution in DMF. After synthesis completion, the resin was well washed with DMF and ether prior to drying. Final cleavages of side chain protecting groups and peptide-resin bonds were performed using Millipore supplied procedure consisting of the following mixture: TFA, water, phenol, triisopropylsilane (88:5:5:2). Peptides were then precipitated and washed with ether prior to drying. Reverse phase HPLC purification (buffer A: TEAP 2.5; buffer B: 80% $CH_3CN$ in A) using a waters prep 4000, absorbance 214 nm, detector model 486, flow rate 50 ml/min.; linear gradient generally from 25 to 60% B in 105 min.) followed by a desalting step (buffer C:0.1% TFA in $H_2O$; buffer D:0.1% TFA in $CH_3CH/H_2O$ 80:20) afforded peptides in yields amounting from 10 to 30% with homogeneity greater than 97% as estimated by HPLC (millennium/photodiode array detection).

The above procedure was used to synthesize seven new GRF analogs of formula A:

X—GRF-peptide    (A)

wherein X is the acyl portion of the corresponding carboxylic acids X-OH synthesized in examples VI, VII, VIII and IX.

| analog | X= |
|---|---|
| 1 | (1R, 2S)-2-ethylcyclopropylacetyl |
| 2 | (+, −)-cis-2-ethylcyclopropylacetyl |
| 3 | (1R, 2R)-2-ethylcyclopropylacetyl |

-continued

| analog | X= |
|---|---|
| 4 | (1:1) mixture of (1S, 3R) and (1R, 3R)-3-methylcyclopentylacetyl |
| 5 | bicyclo[4.1.0]heptylacetyl |
| 6 | 2-methylphenylacetyl |
| 7 | 3-methylphenylacetyl |

EXAMPLE XI

Effect of 8 Different hGRF(1-44)NH$_2$ Analogs on IGF-1 Levels

The objective of this experiment was to compare the effects of 8 different hGRF(1-44)NH$_2$ analogues including TH 9507 on IGF-1 levels following S.C. chronic administration in growing male pigs.

Animal procedures were conducted as described in the protocol GRF-30 submitted Apr. 30, 1999, with the following modification: only 8 GRF analogues, including TH 9507, were provided by the sponsor. Accordingly, the study was performed on 30 pigs.

Laboratory procedures were conducted as follow: IGF-1 levels were measured in pig sera using a commercial kit (DSL-5600) purchased from Diagnostic Systems Laboratories Inc., Tex., USA. Briefly, IGF-1 levels are quantified using a two-site immunoradiometric assay (IRMA) following acid-ethanol extraction.

Statistical analysis: IGF-1 data were subjected to a two-way repeated measures analysis of variance, with time (day 1, 3 or 6) and treatments (A to J) as variation factors pairwise multiple comparison procedures were then run by the Student-Newman-Keuls method. All statistical procedures were performed using the computerized SigmaStat software (Jandel Scientific). A P<0.05 was considered statistically significant.

Figure 7A:
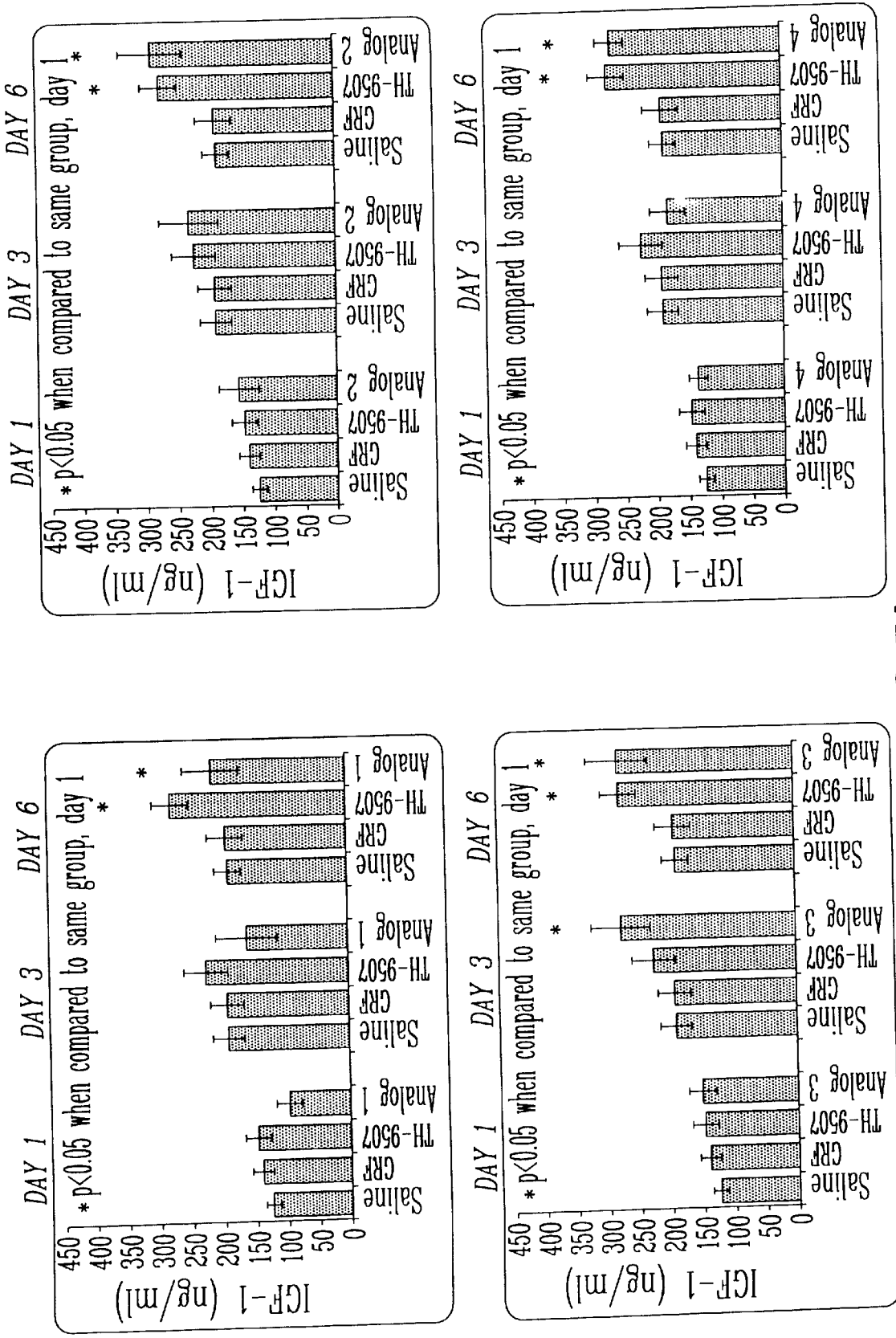

As shown in FIG. 7, neither saline nor hGRF(1-44)NH$_2$-treated animals had any significant variations of their IGF-1 concentrations in the study period. This confirm previous results showing that hGRF(1-44)NH$_2$ is not able to induce any significant increase in IGF-1 levels when injected subcutaneously in pigs twice a day at 10 ug/kg.

All tested analogs (TH 9507 and analogues 1 to 7) significantly increased IGF-1 levels in pigs on day 6, when compared to their basal levels on day 1. Only analogues 3 and 6 significantly increased IGF-1 levels on day 3. No significant difference between analogues was derived from the statistical analysis. However, analogue 6 appeared to exhibit a very strong IGF-1 inducing efficacy, bringing IGF-1 levels up to 358.3±17.1 ng/ml following 5 days of injection (when compared to 190.1±21.0 ng/ml and 279.1±28.4 ng/ml in the saline- and the TH 9507-treated groups, respectively.

These results indicate that all 7 new hGRF(1-44)NH$_2$ analogs tested in the present invention are more potent than the native GRF molecule. This suggests that the attachment of various aliphatic chains on the N-terminal portion of GRF(1-44)NH$_2$ successfully increases its GH-releasing potency.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. An hydrophobic GRF analog of formula A:

X—GRF-peptide    (A)

wherein;
the GRP peptide is a peptide of formula B;

A1-A2-Asp-Ala-Ile-Phe-Thr-A8-Ser-Tyr-Arg-Lys-A13-Leu-A15-Gln-Leu-A18-Ala-Arg-Lys-Leu-Leu-A24-A25-Ile-A27-A28-Arg-A30-R₀    (B)

wherein,
A1 is Tyr or His;
A2 is Val or Ala;
A8 is Asn or Ser;
A13 is Val or Ile;
A15 is Ala or Gly;
A18 is Ser or Tyr;
A24 is Gln or His;
A25 is Asp or Glu;
A27 is Met, Ile or Nle;
A28 is Ser or Asn;
A30 is a bond or any amino acid sequence of 1 up to 15 residues;
$R_0$ is $NH_2$ or $NH-(CH_2)_n-CONH_2$, with n=1 to 12 and;
X is a hydrophobic tail anchored via an amide bond to the N-terminus of the peptide and said hydrophobic tail defining a backbone of 5 to 7 atoms;
  wherein said backbone can be substituted by $C_{1-6}$ alkyl, $C_{3-6}$ cycloalkyl, or $C_{6-12}$ aryl;
  and comprises at least one rigidifying moiety connected to at least two atoms of the backbone;
    said moiety selected from the group consisting of double bond, triple bond, saturated or unsaturated $C_{3-9}$ cycloalkyl, and $C_{6-12}$ aryl
and wherein X is selected from the group consisting of:

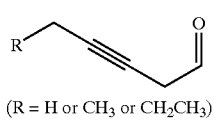
(R = H or CH₃ or CH₂CH₃)

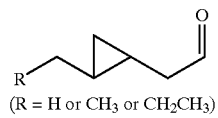
(R = H or CH₃ or CH₂CH₃)

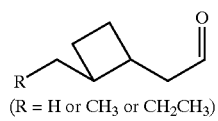
(R = H or CH₃ or CH₂CH₃)

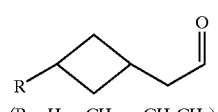
(R = H or CH₃ or CH₂CH₃)

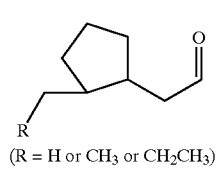
(R = H or CH₃ or CH₂CH₃)

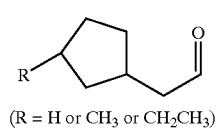
(R = H or CH₃ or CH₂CH₃)

(R = H or CH₃ or CH₂CH₃)

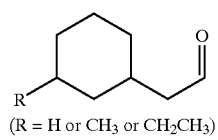
(R = H or CH₃ or CH₂CH₃)

-continued

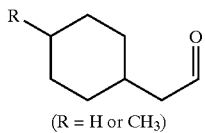

(R = H or CH₃)

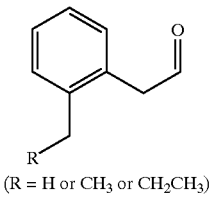

(R = H or CH₃ or CH₂CH₃)

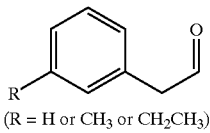

(R = H or CH₃ or CH₂CH₃)

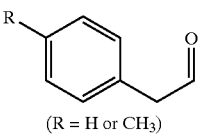

(R = H or CH₃)

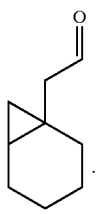

.

2. A pharmaceutical formulation for inducing growth hormone release which comprises as an active ingredient a GRF analog as claimed in claim 1, in association with a pharmaceutically acceptable carrier, excipient or diluent.

3. A method of increasing the level of growth hormone in a patient which comprises administering to said patient an effective amount of a GRF analog as claimed in claim 1.

4. A method for the diagnosis of growth hormone deficiencies in patients, which comprises administering to said patient a GRF analog as claimed in claim 1 and measuring the growth hormone response.

5. A method for the treatment of pituitary dwarfism or growth retardation in a patient, which comprises administering to said patient an effective amount of a GRF analog as claimed in claim 1.

6. A method for the treatment of wound or bone healing in a patient, which comprises administering to said patient an effective amount of a GRF analog as claimed in claim 1.

7. A method for the treatment of osteoporosis in a patient, which comprises administering to said patient an effective amount of a GRF analog as claimed in claim 1.

8. A method for improving protein anabolism in human or animal, which comprises administering to said human or animal an effective amount of a GRF analog as claimed in claim 1.

9. A method for inducing a lipolytic effect in human or animal inflicted with clinical obesity, which comprises administering to said human or animal an effective amount of a GRF analog as claimed in claim 1.

10. A method for the overall upgrading of somatroph function in human or animal, which comprises administering to said human or animal an effective amount of GRF analog as claimed in claim 1.

* * * * *